United States Patent [19]
Conners et al.

[11] Patent Number: 5,960,104
[45] Date of Patent: *Sep. 28, 1999

[54] DEFECT DETECTION SYSTEM FOR LUMBER

[75] Inventors: Richard W. Conners; David E. Kline; Phillip A. Araman, all of Blacksburg; Xiangyu Xiao, Reston; Thomas H. Drayer, Blacksburg, all of Va.

[73] Assignees: Virginia Polytechnic & State University, Blacksburg, Va.; The United States of America as represented by the Secretary of Agriculture, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/707,982

[22] Filed: Aug. 16, 1996

[51] Int. Cl.⁶ .............................. G06T 5/40; G06K 9/34; G06K 9/46; G01N 23/083
[52] U.S. Cl. .......................... 382/141; 382/171; 144/402
[58] Field of Search .................................. 382/108, 110, 382/141, 154, 168, 171, 170, 173; 348/86, 88, 93, 125, 128; 356/371, 376, 381, 372, 406; 364/468.17, 469.01, 507; 250/559.25, 559.05, 559.08, 559.11; 209/517, 518; 144/391, 392, 398, 402, 403, 404, 408

[56] References Cited

U.S. PATENT DOCUMENTS

| | | | |
|---|---|---|---|
| 3,694,658 | 9/1972 | Watson et al. | 250/119 DF |
| 3,856,061 | 12/1974 | Miles | 144/312 |
| 3,976,984 | 8/1976 | Matthews et al. | 356/200 |
| 4,123,169 | 10/1978 | Merilainen et al. | 356/167 |
| 4,149,089 | 4/1979 | Idelsohn et al. | 250/563 |
| 4,188,544 | 2/1980 | Chasson | 250/560 |
| 4,207,472 | 6/1980 | Idelsohn et al. | 250/563 |
| 4,221,974 | 9/1980 | Mueller et al. | 250/563 |

(List continued on next page.)

FOREIGN PATENT DOCUMENTS

| | | |
|---|---|---|
| 1125148 | 6/1982 | Canada . |
| 1146051 | 5/1983 | Canada . |
| 1281392 | 11/1987 | Canada . |
| 0 500 161 A2 | 8/1992 | European Pat. Off. . |
| 2 507 527 | 12/1982 | France . |
| 223 534 | 6/1985 | Germany . |
| 226 383 | 8/1985 | Germany . |
| 265 357 A1 | 3/1989 | Germany . |
| 61-144550 | 7/1986 | Japan . |
| WO 91/05245 | 4/1991 | WIPO ............................ G01N 23/02 |
| WO 93/22659 | 11/1993 | WIPO ............................ G01N 21/89 |
| WO 95/24636 | 9/1995 | WIPO ............................ G01N 21/84 |

*Primary Examiner*—Leo H. Boudreau
*Assistant Examiner*—Brian P. Werner
*Attorney, Agent, or Firm*—Thelen, Reid & Priest, L.L.P.

[57] ABSTRACT

A machine vision system that can address a number of board, lineal, cant, and flitch inspection problems by incorporating all the sensors needed to address the surface feature detection problem, the three-dimensional shape detection problem, and the internal feature detection problem. To detect surface features, two color cameras are employed, one for imaging each of the major faces of a board, lineal, cant, or flitch. To address the three-dimensional shape detection problem, a high speed laser profiling device is employed. An x-ray scanning system is employed to detect internal features. The system is able to process material in a species-independent manner by using a histogram-based segmentation procedure for analyzing both the camera imagery and the x-ray imagery; and can detect small defects by removing the effects of large features from the histograms once they have been detected. The system also utilizes redundant information from the set of multiple sensors to improve system accuracy. The volume of data that must be analyzed due the use of three sets of sensors is reduced by ordering the way the data is analyzed. The laser profile data is processed first, followed by the x-ray data and the color imagery. Finally, the system reduces the required volume of data by incorporating a crack/check preserving filter. This filter is implemented in special purpose hardware, and filters the color imagery as it is collected.

19 Claims, 6 Drawing Sheets

U.S. PATENT DOCUMENTS

| | | | |
|---|---|---|---|
| 4,245,913 | 1/1981 | Sarlos | 356/431 |
| 4,246,940 | 1/1981 | Edwards et al. | 144/209 A |
| 4,286,880 | 9/1981 | Young | 356/431 |
| 4,468,992 | 9/1984 | McGeehee | 83/56 |
| 4,500,835 | 2/1985 | Heikkila | 324/58.5 R |
| 4,514,680 | 4/1985 | Heikkila et al. | 324/58.5 |
| 4,541,722 | 9/1985 | Jenks | 356/376 |
| 4,606,645 | 8/1986 | Matthews et al. | 356/446 |
| 4,607,212 | 8/1986 | Jakkula | 324/58.5 R |
| 4,794,963 | 1/1989 | Oppeneer | 144/358 |
| 4,805,679 | 2/1989 | Czinner | 144/357 |
| 4,827,142 | 5/1989 | Hatje | 250/563 |
| 4,831,545 | 5/1989 | Floyd et al. | 364/507 |
| 4,879,752 | 11/1989 | Aune et al. | 382/1 |
| 4,891,530 | 1/1990 | Hatje | 250/572 |
| 4,916,629 | 4/1990 | Bogue et al. | 364/507 |
| 4,926,350 | 5/1990 | Bechtel et al. | 364/550 |
| 4,931,657 | 6/1990 | Houston et al. | 250/559 |
| 4,934,229 | 6/1990 | Greten et al. | 83/75.5 |
| 4,941,357 | 7/1990 | Schajer | 73/600 |
| 4,965,734 | 10/1990 | Edwards et al. | 364/474.09 |
| 4,984,172 | 1/1991 | Luminari | 364/478 |
| 4,992,949 | 2/1991 | Arden | 364/478 |
| 5,023,805 | 6/1991 | Aune et al. | 364/468 |
| 5,042,341 | 8/1991 | Greten et al. | 83/75.5 |
| 5,142,955 | 9/1992 | Hale | 83/75.5 |
| 5,252,836 | 10/1993 | Matthews et al. | 250/571 |
| 5,257,101 | 10/1993 | Lee | 358/101 |
| 5,394,342 | 2/1995 | Poon | 364/558 |
| 5,412,220 | 5/1995 | Moore | 250/563 |
| 5,703,960 | 12/1997 | Soest | 382/141 |

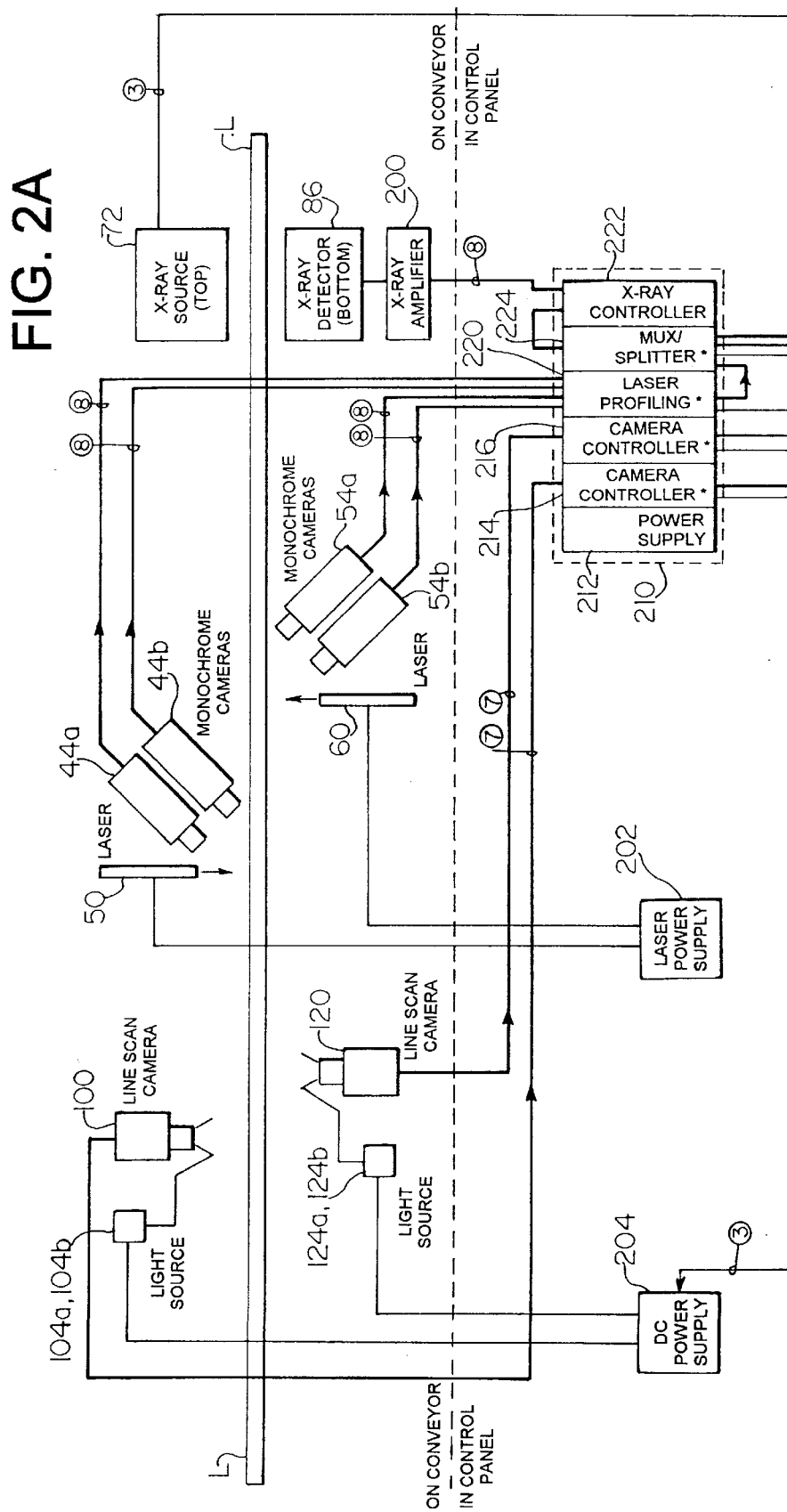

DEFECT DETECTION SYSTEM FOR LUMBER

BACKGROUND OF THE INVENTION

1. Field of the Invention

The present invention relates to the detection of defects in lumber. More specifically, the invention relates to a defect detection system which uses a combination of technologies to inspect a wood board (flitch) to determine the presence and location of defects to optimize cutting of the board.

2. Related Art

Wood is the primary material from which many high-demand products are made. It is used as a structural building material, e.g., the material used to create 2×4s, 2×8s, and 2×12s used in framing; as a finishing building material, e.g., a material used to create trim used around doors and windows as well and a material used to fabricate doors and windows; as a packaging material, e.g., a material used to create pallets and enclosures; and as a material in making finished products, e.g., a material used to create furniture and cabinets.

The forest products industry can be broken down into a number of possible processing operations. The first operation involves cutting trees and turning them into logs. This processing operation is called logging. A second processing operation involves turning logs into a product that can be used by others. This processing operation is called primary processing or primary manufacturing. Examples of primary processing operations include sawmillers that turn logs into lumber, plywood manufacturers that turn logs into plywood, and veneer manufacturers that turn logs into veneers. A third processing operation involves turning the products created by primary manufacturers into products that are typically sold to end users, i.e., the buying public. This processing operation is called secondary processing or secondary manufacturing. Example products created by secondary manufacturers include doors, windows, cabinets, furniture, flooring, trim, and other household fixtures.

Forest products companies typically concentrate their efforts in one particular type of processing operation, i.e., a company is typically involved in either logging; or in one or more areas of primary processing; or in one or more areas of secondary processing. To accommodate this structure, rules have been established for determining the value of logs to facilitate acquisition of logs by primary manufacturers, for determining the value of lumber to facilitate the acquisition of lumber by secondary manufacturers, etc. These rules establish the grade of the material. The higher an item's grade, the higher its market value. Obviously, the end products purchased directly by consumers are not subject to grading rules, but rather individual judgments about what is aesthetically pleasing and what constitutes quality construction.

As with any other manufacturing industry, there is always a trade-off between quality and yield; the higher the quality of a product produced, the fewer the items that can be made from a given volume of raw material. The right trade-off point is, by definition, the one that optimizes the value of all the products produced from a given volume of raw material.

As perhaps in no other industry, workers' decisions markedly affect both the quality and yield of products created. Consider just the sawing operations performed in each of the above-mentioned three basic processing operations. The sawyer's goal is to remove defects from the wood material while maximizing the volume of the product produced, where a defect is defined to be any feature in wood that will affect the quality/grade of the product being produced. Sawyers typically make hundreds of sawing decisions during a given work day, each of which can and does affect the quality and volume of product produced. Where applicable, human graders make hundreds of grading decisions each work day, decisions that directly affect the market value of the items inspected. Studies have shown that employees do not always make the best decisions in saw-up processes or are not always right in their grade assignments. These errors cost manufacturers money.

Researchers from government, universities, and industry have recognized the need for automation in the forest products industry for a number of years. Hence, a good deal of work has gone into creating devices for aiding in, if not totally automating, the sawing and grading processes involved in the forest products industry. Clearly, if one is to automate any of these processes, one must develop machine vision technologies capable of locating and identifying defects. Research aimed at creating such machine vision technologies has resulted in the publication of a number of articles in the scientific literature and the issuance of a number of patents. These patents are based solely, or in part, on the sensing and processing technologies used to find defects.

To understand the nature of the present invention one must understand the scope and limitations of the work that has previously been done, for example by reviewing the available literature in an application-specific manner. The applications which are thus considered are, in order, (1) logging applications, (2) the primary processing applications, and (3) applications within the secondary manufacturing area.

There are two primary applications for machine vision technology within the logging industry. The first involves analyzing a tree stem to determine where cuts should be made to saw it into logs. Accurately making this decision involves analyzing the three-dimensional shape of the stem and inferring where log grading defects occur within the stem. A second, related application is accurately assigning the appropriate grade to the logs that are created. This problem also involves consideration of a log's three-dimensional shape and a determination of the locations of internal grading defects.

The two primary applications in the logging industry are very similar to an application in the primary processing area. This application in the primary processing area involves determining for a given log the best break-down strategy for creating either lumber or veneer. In both instances, the objective of the strategy is to maximize the value of the products that are created. In either case, the three-dimensional space must be considered, as well as the location and identity of internal grading defects. It should be noted that features affecting a log's grade are also, by and large, the features that affect the grades of lumber and veneer.

A number of researchers and inventors have developed machine vision technologies to scan external and internal features of logs. As discussed by E. M. Williston, *Computer control systems for log processing and lumber manufacturing* (San Francisco, Calif.: Miller Freeman Publications, 1985) ("Williston"), the most widely used log scanners in the forest products industry measure only external features and employ some type of log profile sensor. For many years, applications have been proposed to locate internal log features such as knots, decay, and pith. Examples of such applications are discussed by P. O. G. Hagman et al., "Classification of Scots pine (Pinus sylvestris) knots in density images from CT scanned logs," 53 *Hols als Roh- und Werkstoff*, pp. 75–81 (1995); B. V. Funt et al., "Detection of internal log defects by automatic interpretation of computer tomography images," 37 *Forest Products Journal*, pp. 56–62 (1987); F. W. Taylor et al., "Locating knots by industrial tomography—A feasibility study," 34 *Forest Products Journal*, pp. 42–46 (1984); S. J. Chang, "External and internal defect detection to optimize cutting of hardwood logs and lumber," Transferring Technologies for Industry, No. 3 (USDA, Beltsville, Md., September 1992); and P. A. Araman et al., "Machine vision systems for processing hardwood lumber and logs," 6 *AI Applications*, pp. 13–26 (1992) ("Araman et al."). Several recent patents also disclose scanning technologies for external and internal log features. See, for example, U.S. Pat. Nos. 4,246,940 and 4,965,734 to Edwards et al.; U.S. Pat. No. 4,831,545 to Floyd et al.; U.S. Pat. No. 5,023,805 to Aune et al.; U.S. Pat. No. 5,394,342 to Poon; and International Pat. publication No. WO 91/05245 to Sikanen et al. Commercial applications of these technologies are limited to systems that scan only the external shape of the log. This is primarily due to the very high cost of internal log scanning systems, as well their limited throughput capabilities.

There are two other related applications within the primary processing area, applications that are very different from those described above. The first of these involves log break-down. Logs can be broken down into a number of components including lumber, veneer, cants, and chips. The objective in primary processing is to decide how best to break down a log such that maximum value is attained. Typically, lumber and/or veneer are the products of choice, because they are the products with the highest market value. Maximizing volume of these products is not always analogous to maximizing value, because some grading rules for either lumber or veneer are such that they can be trimmed to a smaller size, yielding a higher-grade, higher-value product. The complexity of grading rules, along with dynamic changes in product pricing, makes it very difficult to maximize product value. Therefore, it is appropriate to be able to know the three-dimensional profile (e.g. size and shape) of the material, along with the location of grading defects on the surface of the material being processed.

Finally, an optimizing system should be able not only to locate grading defects, but also to be able to identify the type of defect present at each location. Adding the ability to classify the type of defect present further improves the quality of the processing decisions that can be made, ensuring that maximum value products can be attained.

The second related primary processing application involves accurately assigning a grade to the product produced (e.g., lumber or veneer). This application does involve some consideration of three-dimensional profile, e.g., the size, shape, and the presence of wane or holes. It also involves the inspection of product surfaces, i.e., the major faces of lumber, veneer flitches, plywood, etc. This assignment of grade generally does not involve the consideration of locations and identities of internal defects, though this is required if one is going to adequately address certain structural lumber and plywood grading problems.

Researchers have for some time understood the importance of creating methods for automating primary processing tasks. In particular, a good deal of work has gone into automating the edging and trimming operations done to create softwood structural lumber. Most of this work has concentrated on using laser ranging devices or optical profiling devices to locate board profile or wane on softwood flitches, as discussed by Williston, and has resulted in several patents, most notably U.S. Pat. No. 4,541,722 to Jenks; U.S. Pat. No. 4,188,544 to Chasson; U.S. Pat. No. 5,142,955 to Hale; U.S. Pat. No. 4,468,992 to McGeehee; U.S. Pat. No. 4,123,169 to Merilainen et al.; U.S. Pat. No. 4,207,472 to Idelsohn et al.; U.S. Pat. No. 4,221,974 to Mueller et al.; and U.S. Pat. No. 4,794,963 by Oppeneer. Commercial systems based on these patents are available for optimizing lumber production from flitches or cants, primarily for softwood lumber production. These commercial systems are based solely on board profile information; hence, these systems clearly cannot provide optimal performance where surface defects such as knots have a large influence on product value.

To detect those defects in wood that influence product value, much effort has also gone into lumber defect scanning systems, particularly in the production of structural softwood lumber. These systems, described by R. Szymani et al., "Defect detection in lumber: State of the art," 31 *Forest Products Journal*, pp. 34–44 (1981) ("Szymani et al."), employ scanning techniques including optical, slope-of-grain, microwave, ultrasonic, and x-ray sensing techniques. Optical scanning is disclosed in U.S. Pat. No. 4,286,880 to Young; U.S. Pat. No. 5,412,220 to Moore; U.S. Pat. No. 4,827,142 to Hatje; International Pat. publication No. WO 93/22659 to Nyquist; and International Pat. publication No. WO 95/24636 to Astrom et al. Slope-of-grain detection is disclosed in U.S. Pat. No. 4,926,350 to Bechtel et al.; U.S. Pat. No. 4,500,835 to Heikkila; and U.S. Pat. Nos. 3,976,384, 4,606,645 and 5,252,836 to Matthews et al. Microwave sensing is disclosed in U.S. Pat. No. 4,607,212 to Jakkula and U.S. Pat. No. 4,514,680 to Heikkila et al. X-ray scanning is disclosed in U.S. Pat. No. 4,941,357 to Schajer and E. German Patent No. 223 534 to Fischer et al. While each of these systems is specifically focused on detecting a particular feature in wood, none of these can precisely detect and classify all features that affect the value of lumber.

More recent systems in softwood lumber production and grading have been proposed to more precisely locate critical strength-reducing defects in lumber based on a combination of optical sensing techniques with one or more of the following: x-ray scanning, microwave scanning, deflection testing, capacitance sensing, and ultrasound. Such systems are described by Szymani et al.; D. J. Kenway et al., "Computer aided lumber grading," *Proceedings of the 7th Symposium on Nondestructive Testing of Wood* (Madison, Wis. 1990) ("D. J. Kenway et al."); and J. E. Aune, "X-ray edger-optimizer makes money at MacMillan Bloedel's Alberni Pacific Division," *4th International Conference on Scanning Technology in the Wood Industry* (San Francisco 1991). Patents relating to research in this area combine optical profiling with x-ray scanning (disclosed in U.S. Pat. No. 4,879,752 and Canadian Pat. No. 1,281,392 to Aune et al.) and optical scanning with deflection testing (disclosed in U.S. Pat. No. 4,805,679 to Czinner). Even though these multi-sensor defect detection approaches can more precisely locate strength-reducing defects in wood, they have not been successfully used to detect all lumber surface features that affect its appearance quality.

While one softwood company is providing customers with machine evaluated lumber (MEL), there is no commercial system available that can structurally grade softwood lumber based on the location and identity of features in the wood as established by the Southern Pine Inspection Bureau, Western Wood Products Association, etc.

In hardwood lumber, it is the visual appearance of wood, rather than its strength, that affects its value. Some research has been performed to create systems for automating primary processing and grading of lumber, as described by Araman et al. and by R. W. Conners et al., "A machine vision system for automatically grading hardwood lumber," 2 *Industrial Metrology*, pp. 317–342 (1992) ("R. W. Conners et al. (I)"). However, no practical devices have been designed for solving either the edging and trimming optimization problem or the grading problem. Some hardwood sawmillers are using devices designed for softwood edging and trimming in their hardwood plants. These systems are costly and provide substantially suboptimal strategies for hardwood lumber processing and grading where visual appearance defects have a substantial affect on product value.

Researchers have also investigated the softwood plywood processing and grading problem, as discussed by D. A. Butler et al., "An adaptive image preprocessing algorithm for defect detection in Douglas-fir veneer," 43 *Forest Products Journal*, pp. 57–60 (1993); J. B. Forrer et al., "Image sweep-and-mark algorithms. Part 2. Performance evaluations," 39 *Forest Products Journal*, pp. 39–42 (1989); and C. R. Friedrich, "Development and simulation of machine automated green veneer sorting and defect identification," 4th *International Conference on Scanning Technology in the Wood Industry* (San Francisco 1991). Patent disclosures relating to commercial softwood veneer inspection include U.S. Pat. No. 3,694,658 to Watson et al. and U.S. Pat. No. 4,984,172 to Luminari. These patented systems can only detect defects involving discontinuities in the wood (holes, splits, voids, etc.). Surface defects such as knots, stains, and other such sound features cannot be reliably detected by these systems.

Finally, there are the applications within the secondary manufacturing area. The process of turning dried wood and veneer into a finished product is, as one might suppose, a difficult task, typically requiring a good number of processing operations. For purposes of this discussion, most work on developing machine vision technologies for aiding this industrial sector has concentrated on the initial sawing operations performed to turn lumber into the rough parts used to create all the components of the finished product. The place where this cutup occurs in a secondary manufacturing plant is called the rough mill.

Depending on the dimensions of the rough parts needed, rough mills are usually laid out in one of two ways. The first, more modern layout involves first sawing lumber into the desired widths needed using a gang-rip saw. The resulting lumber strips or lineals are then crosscut to the desired lengths. A second layout involves first crosscutting the lumber into the required lengths. This crosscutting operation is then followed by ripping each of the parts sawn to length into the parts that have the required widths. Obviously, in either instance the objective is to remove any undesirable wood features while maximizing yield.

Since the lumber raw material used by secondary manufacturers has already had a good deal of value added to it by the loggers and the primary manufacturers, the cost of this raw material is relatively high as compared to the raw materials used by primary processors. Because of the cost of raw material, a good deal of research effort has been expended to develop machine vision technologies to optimize the utilization of lumber. This research has been described by P. A. Araman et al.; R. W. Conners et al. (I); C. C. Brunner et al., "Using color in machine vision systems for wood processing," 22 *Wood and Fiber Science*, pp. 413–428 (1990); P. Klinkhachorn et al., "Prototyping an automated lumber processing system," 43 *Forest Products Journal*, pp. 11–18 (1993); A. J. Koivo et al., "Automatic classification of surface defects on red oak boards," 39 *Forest Products Journal*, pp. 22–30 (1989); C. W. McMillin, "Application of automatic image analysis to wood science," 14 *Wood Science*, pp. 97–105 (1982); C. W. McMillin et al., "ALPS—A potential new automated lumber processing system," 34 *Forest Products Journal*, pp. 13–20 (1984); R. W. Conners et al., "Identifying and locating surface defects in wood: Part of an automated lumber processing system," *IEEE Transactions on Pattern Analysis and Machine Intelligence*, vol. PAMI-5, pp. 573–583 (1983) ("R. W. Conners et al. II"); and R. W. Conners et al., "The utility of color information in the location and identification of defects in surfaced hardwood lumber," 1st *International Conference on Scanning Technology in Sawmilling* (San Francisco, Calif. 1985) ("R. W. Conners et al. III").

Some of this research has found its way into commercial systems. However, these systems are typically based on a single sensing modality, e.g., one or more black-and-white cameras or one or more color cameras, and are only capable of sensing gross features in wood. Examples of applications where this is sufficient include the defect detection system for a gang rip saw and/or the cross cutting of softwood lumber for some product applications. It should be kept in mind that the automatic detection of features in softwood lumber is considered by researchers to be simpler problem than the automatic detection of features in hardwood.

A thorough review of the literature reveals that while rough mill automation can be economically justified, no commercial system is currently available that can automatically inspect lumber and detect all features that are necessary to completely optimize yield in the rough mill. State-of-the-art commercial systems still rely on operators to inspect lumber for critical defects. For example, state-of-the-art cross cut saws still rely on operators to mark defects with florescent crayons prior to cutup.

The prior art systems discussed above dealing with defect detection in primary processing and grading of lumber might have some applicability to defect detection for rough mill applications. However, in secondary lumber processing, a completely automatic lumber inspection system must not only accurately detect the size and shape of lumber, but also must accurately find the location and type of defect with sufficient precision and resolution. As mentioned earlier, none of the patented scanning technologies are robust enough to provide this level of detail in lumber defect identification. With wood being a very non-homogeneous and highly variable material, machine vision systems that can reliably detect lumber features have not yet been achieved.

To address the need for such robust machine vision systems for the lumber inspection problem, a combination of sensing methods must be applied. This fact was realized in 1981 by R. Szymani et al. Within the last five years, computing technology has made such a multi-sensing approach for lumber inspection a more realizable goal. Several researchers have worked in the area of multi-sensor scanning, as discussed by D. J. Kenway et al.; R. W. Conners et al. (I); J. F. Portala et al., "Nondestructive testing techniques applied to wood scanning," 2 *Industrial Metrology*, pp. 299–308 (1992); P. Rowa, "Automatic visual inspection and grading of lumber," 1st *International Seminar on Scanning Technology and Image Processing on Wood* (Luleå University, Skelleftea Sweden 1992); and O. Hagman et al., "Multivariate image analysis methods to classify features on scots pine: Evaluation of a multisensor approach," 5th *International Conference on Scanning Technology and Pro-* cess Control for the Wood Products Industry (San Francisco, Calif. 1993). Although some of the multi-sensor systems dealing with defect detection in primary processing and grading of lumber (for example, U.S. Pat. No. 4,879,752 and Canadian Pat. No. 1,281,392 to Aune et al.; U.S. Pat. No. 4,805,679 to Czinner) can be applied to rough mill automation, they still are not able to provide the precision and accuracy needed to detect all critical lumber defects.

From the above it should be clear that, in general, the automatic inspection of boards, lineals, cants or flitches requires three types of information, as described by R. W. Conners et al., "Developing a multi-sensor scanning system for hardwood inspection and processing," *Proceedings from the 2nd International Seminar/Workshop on Scanning Technology and Image Processing on Wood* (Skelleftea, Sweden 1995). First, automatic inspection requires information about the three-dimensional shape of the board, lineal, cant, or flitch. This information is needed to determine whether the object inspected is warped, contains wane, or contains areas that are too thin. Second, it requires information about the location and identity of internal features that, during further processing, could be exposed and make the processed part either unsuitable for further use or of decreased value. Finally, it requires information about the location and identity of surface features and/or discolorations. This last type of information is particularly important in many hardwood applications where the appearance of the product plays such an important role. Unfortunately, no single sensing modality can provide all of this needed information.

Perhaps the most mature technology for inspecting wood is that which can measure a board's, lineal's, cant's, or flitch's three dimensional profile. Patents which address the acquisition of this type of information include U.S. Pat. No. 4,123,169 to Merilainen et al., U.S. Pat. No. 4,188,544 to Chasson, U.S. Pat. No. 4,541,722 to Jenks, U.S. Pat. No. 4,984,172 to Luminari, U.S. Pat. No. 5,142,955 to Hale, International Patent No. WO 93/22659 to Nyquist, and E. German Patent No. 265 357 to Fischer et al. While these single sensing modality devices can gauge three-dimensional shape at varying degrees of resolution, they do not address ways for locating and identifying surface and/or internal features in wood. Surface and/or internal features present in a board, lineal, cant, or flitch are, in many cases, used to establish its value. Hence, these systems are seriously limited as to the types of inspection tasks they can perform.

As to the internal features of boards, lineals, cants, or flitches, a number of single sensor systems for addressing this issue have also been developed, including system which employ two different types of electromagnetic radiation sensing techniques. The first type uses microwaves. Microwave-based systems include U.S. Pat. No. 4,500,835 to Heikkila, U.S. Pat. No. 4,514,680 to Heikkila et al., and U.S. Pat. No. 4,607,212 to Jakkula. A fundamental problem with microwaves is that they cannot be used to detect any feature that has a diameter smaller than the wavelength of the radiation being employed. Hence, microwave-based systems have difficulty detecting features smaller than approximately ¼ inch (0.635 cm) in diameter. Unfortunately, for most wood inspection tasks features of this size can and do play an important role in establishing value. Hence these systems are also very limited in the number of applications on which they can be used.

The second type uses x-rays. A number of single sensor x-ray systems have been developed, as exemplified in U.S. Pat. No. 4,941,357 to Schajer and E. German Patent No. 223 534 to Fischer et al. These systems employ a single x-ray source and set of detectors that take a single view of the object being inspected. One very fundamental limitation of this approach is that the system cannot distinguish areas of wane from areas of decay. This limitation markedly limits their utility in addressing the more general wood inspection problem.

A variation of the above x-ray-based approaches is described in International Patent No. WO 91/05245. This invention uses computed tomography (CT) to locate and identify features. That is, it uses x-rays to take several views of an object. These views can then be used to reconstruct a cross-section of the object. Consequently, this system can provide information not only about internal features but also about surface features and three-dimensional shape.

Unfortunately, this approach has a number of limitations. First, the throughput is limited by the need to take several views and the need to do reconstruction. CT reconstruction methods are fairly complex computationally, and require relatively expensive special purpose hardware. For these same reasons CT systems are expensive, too expensive for most application problems. Lastly, CT cannot sense color variations in an object and, hence, does not address this very important part of the wood inspection problem. The limitations in throughput, cost, and the inability to detect discoloration mean that CT-based approaches are not acceptable for most wood inspection problems.

As to the detection of surface features, a number of systems have been developed for this task, all employing only a single sensing modality. The sensors of choice are black-and-white cameras and color cameras. U.S. Pat. No. 4,827,142 to Hatje and U.S. Pat. No. 5,412,220 to Moore describe systems that employ such cameras. The major problems with these systems are that they cannot determine three-dimensional profile and they cannot locate and identity internal wood features.

Another problem is their innate lack of feature detection and identification accuracy. For example, many species of wood contain knots that are almost the same color as clear wood. Such knots pose problems for black-and-white camera or color camera-based systems. There are commercially available black-and-white camera-based systems for automating the gangrip operation in rough mills. These systems only have to locate and identify major defects and even if some errors are made, they do provide performance improvements over systems that perform the gangrip based solely on board edge information. Clearly, these single sensor-based systems cannot determine three-dimensional shape nor can they be used to locate and identify internal defects. They therefore address only part of the general inspection problem.

U.S. Pat. No. 3,694,658 to Watson et al. describes a system based on a black-and-white camera sensor. However, this system uses back lighting, lighting that does not illuminate the surface of the material that can be imaged by the camera. This invention's use of back lighting results from the desire to detect holes in veneer. Clearly, this technology is not applicable to wood surface defect detection problem. Similarly, as described in U.S. Pat. No. 4,468,992 to McGeehee, a system uses back lighting and an optical detector to measure only the width of a board. The capabilities of such a system are very limited in the area of general wood inspection.

A variant of the standard black-and-white/color camera-based systems is a system based on the so-called smart sensor, International Patent No. WO 95/24636. This smart sensor can gauge three-dimensional shape information while it is generating black-and-white imagery. As such, it does offer an improvement over the above. However, this sensor still has difficulties with knots that are the same color as clear wood and, of course, this sensor cannot be used to locate and identify internal defects. This imposes limitations on any system that uses only this scanning modality.

Yet another variant on the basic black-and-white/color camera-based systems, is the one described in U.S. Pat. No. 4,207,472 to Idelsohn et al. and U.S. Pat. No. 4,221,974 to Mueller et al. This system uses a flying-spot of laser light to illuminate board surfaces. Imagery is generated using photo diodes to sense the light. By carefully controlling the speed of the laser spot and the times at which the photo diodes are read, two-dimensional black-and-white image data can be collected,. Because this data is similar in content to that generated by a black-and-white camera, this system suffers from the same problems discussed above for single sensor black-and-white-based systems.

Another, totally different approach to surface feature location and identification involves the use of sensors that can detect the slope-of-grain. Systems based on slope-of-grain detection sensors include U.S. Pat. No. 3,976,384, U.S. Pat. No. 4,606,645, and U.S. Pat. No. 5,252,836 to Matthews et al., and U.S. Pat. No. 4,926,350 to Bechtel et al. These systems also have limitations. First, they cannot determine three-dimensional shape. Second, they cannot locate and identify internal defects. Finally, they are unable to detect the important discolorations that occur in wood.

The realization that no single sensing technology is adequate for wood inspection has motivated inventors to create systems that employ multiple sensing modalities. For example, the system described in U.S. Pat. No. 4,805,679 to Czinner employs a black-and-white camera together with a device for measuring the modulus of elasticity. While this system might be useful for some wood inspection applications, it is very limited by its inability to determine three-dimensional shape and locate and identify internal features.

Yet another multiple sensor system is described in U.S. Pat. No. 4,831,545 to Floyd et al. This system employs the slope-of-grain detection sensor described in U.S. Pat. No. 4,606,645 to Matthews ct al. with a sensor for detecting wane, i.e., a sensor for gauging rough three dimensional shape. This system has a number of problems with regard to the general wood inspection problem. First, even with the addition of the second sensor, it still cannot determine certain types of warp or areas that are too thin. Second, it cannot locate or identify internal features. Third, it cannot detect surface discolorations. This limits the number of applications to which this technology can be applied.

Three other, seemingly related, multiple sensor systems are described in U.S. Pat. Nos. 4,879,752 and 5,023,805 to Aune et al., U.S. Pat. No. 5,394,342 to Poon, and Canadian Patent No. 1,281,392. U.S. Pat. No. 5,023,805 and U.S. Pat. No. 5,394,342 describe a system for inspecting logs. This system employs two different sensing modalities. It uses a laser-based system to determine three-dimensional log shape and three x-ray sources looking at the log from three different directions to locate internal knots. U.S. Pat. No. 4,879,752 and Canadian Patent No. 1,281,392 describes a system for lumber inspection. This system uses a profiler for finding wane and an x-ray source to find defects in lumber. The lumber inspection system is limited because it cannot detect whether a feature is a surface feature or a purely internal feature, an important differentiation in some applications, nor can this system determine areas of discoloration. Hence, it, too, is limited in the variety of applications in which it can be used.

It is to the solution of these and other problems that the present invention is addressed.

SUMMARY OF THE INVENTION

It is the primary object of this invention to build on this prior art by creating a unique machine vision system that can address a number of board, lineal, cant, and flitch inspection problems.

The present invention achieves this object in a number of ways. First, it incorporates all the sensors needed to address the surface feature detection problem, the three-dimensional shape detection problem, and the internal feature detection problem. To detect surface features this invention employs two color cameras, one for imaging each of the major faces of a board, lineal, cant, or flitch. To address the three-dimensional shape detection problem this system employs a high speed laser profiling device. This device can detect not only wane, but also areas which are too thin. Lastly, it employs an x-ray scanning system to detect internal features.

Because the system is designed to address a number of different inspection problems, the second unique feature of the system is that it is able to process material in a species-independent manner. It does so by using a histogram-based segmentation procedure for analyzing both the camera imagery and the x-ray imagery. This approach is based upon the realization that most of a board is clear wood. Hence, defects represent deviations from the properties of clear wood. Therefore, the segmentation method considers the largest peak in the histogram to be caused by the characteristics of clear wood, and looks for deviations from these characteristics by looking for inflection points in a smoothed histogram. No matter what color the clear wood is or what its density distribution is, the segmentation methods can segment out variations from the norm as being features of interest. This particular segmentation approach has been shown to be very robust in university-conducted research on the analysis of black-and-white image data (see R. W. Conners et al. (I)). The experimentation done by the present inventors in developing the present invention clearly shows that the segmentation approach works equally well on x-ray image data, a fact which was not previously known or recognized in the prior art, to the best knowledge of the present inventors.

One difficulty with this histogram-based procedure is that the characteristics of large wood features can overwhelm the characteristics of smaller wood features, making them undetectable. This is one of the reasons that the system of Aune et al. (U.S. Pat. No. 4,879,752 and Canadian Patent No. 1,281,392), described above, has difficulty detecting small defects. A third unique feature of this invention is its enhanced ability to detect small defects by removing the effects of large features from the histograms once they have been detected. This allows the previously overwhelmed characteristics of smaller features to finally show themselves in the histogram data.

Developing systems to accurately locate and identify features in wood has proven to be a difficult task. Therefore, a fourth unique feature of this invention is that it utilizes redundant information from the set of multiple sensors. This redundancy is utilized in this invention to improve system accuracy. Of the existing multiple sensor systems described above, only those systems that use an x-ray scanner and a profiler generate redundant data. The concept of redundant data is based on the fact that the information obtained by the x-ray scanner is dependent on shape (in the case of logs) or thickness (in the case of boards). Hence, considering the shape or the thickness of an object helps in understanding the data generated by the x-ray scanner. No existing multiple sensor system exploits this redundancy. Previous systems employing profile systems and x-ray systems process the collected image data independently, combining the results only after all the image analyses have been completed. In the case of the prior art log scanning systems, information about the shape of the log is combined with independently derived information about the locations of knots in the log. In the case of the prior art board inspection systems, identified areas of wane are combined with independently-derived locations of knots in the board. Such independently-combined information is then used to optimize subsequent log or board processing. Such independent processing of images limits the accuracy and speed of the image analysis algorithms employed.

To help improve the accuracy of the results, this invention attempts to exploit all the possible redundancies that exist in the multiple sensor data. For example, a knot is denser than clear wood, a fact that allows possible knot locations to be found in x-ray imagery. A knot is also a round, brown area in the color imagery. Hence, the confidence that a particular area on the board is a knot increases, if this area is both denser than clear wood and a round brown spot. Such redundancy checks are not performed in the above-described prior art systems primarily because measures to determine such redundancy do not exist in the sensor arrays they employ.

A fifth feature of this invention addresses another important problem. While it is known that multiple sensors are needed to gauge all information required to address the general board, lineal, cant, or flitch inspection problems, each new sensor increases the volume of data that must be analyzed. Given the throughput requirements of forest products manufacturing facilities, the analysis of this additional data in real-time can cause problems for any automatic inspection system. This invention addresses this problem by ordering the way the data is analyzed. The laser profile data is processed first. Areas of a board, lineal, cant, or flitch either fall above or below an acceptable level of thickness. Hence, the analysis of this profile data is fairly straightforward. Once areas with insufficient thickness are found, these areas are removed from consideration in the subsequent analysis of the x-ray image data and the color image data. Removing these obvious areas of insufficient thickness from subsequent consideration in the analysis of the x-ray data saves computation time. Similarly, areas that are found to be less dense than clear wood in the x-ray data must either be internal voids or decay. Such areas of insufficient density are then removed from further consideration in the color image data. Finally, the color imagery is processed. Color imagery is much more data intensive than either of the two imaging modalities because three pieces of information are needed to characterize each color picture element, i.e., the red response, green response, and blue response. Hence, removing areas from consideration in the analysis of the color image data can markedly reduce computational time.

Finally, for a variety of reasons the color imagery is the highest resolution sensing modality used by the invention. As such, color is the sensing modality that must be used to find small cracks or other fine features that affect the value of the material being processed. Because many applications require very small cracks or checks to be found and removed from boards, lineals, cants, or flitches, very high resolution color camera data has to be collected. This can markedly affect the time required to perform the analysis. A sixth feature of this invention is reduction of the required volume of data by incorporating a crack/check preserving filter. This filter is implemented in special purpose hardware, and filters the color imagery as it is collected. Basically, this filter is applied as disjoint N×M sub-arrays of the color imagery, sub-arrays that in totality completely cover the color image. The filter finds the color pixel in each sub-array that has the darkest color. This color is then chosen to represent the whole N×M sub-array. Using this filter effectively reduces the number of color pixels that has to be collected in each row by a factor of N, and reduces the number of color pixels that has to be collected in each column by a factor of M, while preserving the level of detail needed to locate and identify small cracks or checks.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
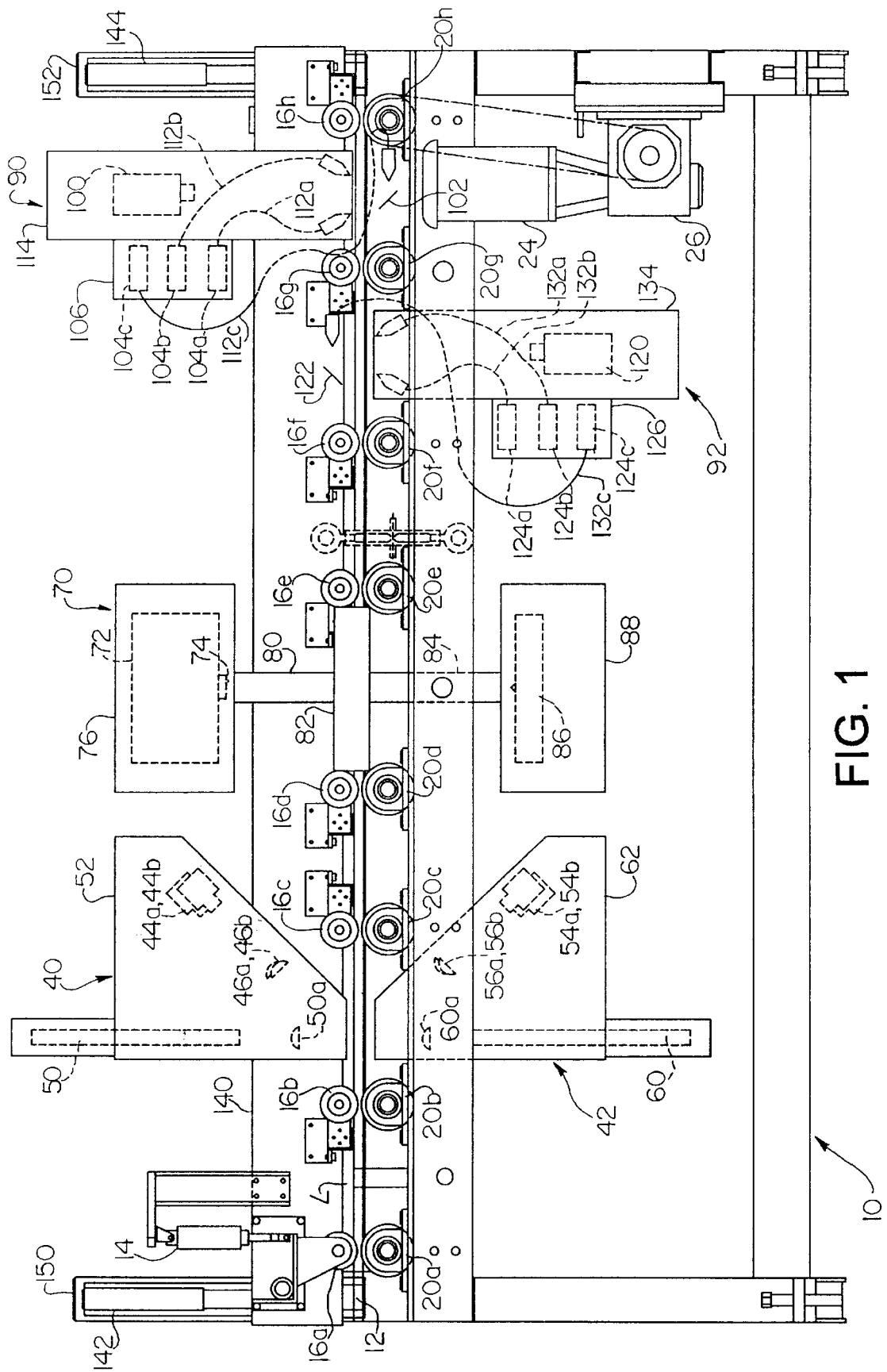
FIG. 1 is a side elevational view of an embodiment of the mechanical components in accordance with the present invention, for the cross-cutting of lineals.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Referring now to FIG. 1, there is shown an embodiment of the apparatus 10 in accordance with the present invention for the cross-cutting of lineals L. As viewed in FIG. 1, lineals L move from left to right through the apparatus 10. They enter at standard optical object detection system 12, which senses the presence of a lineal L entering the apparatus 10. This causes the activation of a pneumatic piston assembly 14, which is operatively connected to a gripper roller 16a to depress a first gripper roller 16a, effectively engaging the lineal L against a first drive roller 20a.

Gripper roller 16a is one of a plurality of gripper rollers 16a–16h which are positioned opposite corresponding drive rollers 20a–20h, to keep the lineal L effectively engaged with the drive rollers 20a–20h. Drive rollers 20a–20h are positioned to engage the lower face of a lineal L to move a lineal L through the apparatus 10. Each of the gripper rollers 16a–16h is spring loaded to provide the needed downward pressure on the lineal L.

Drive rollers 20a–20h are all conventionally linked together by drive belts (not shown) and are powered by the electric motor 24. The power supplied by the motor 24 is supplied to a transmission 26 to gear down the rotational speed of rollers 20a–20h. The drive rollers 20a–20h are rubber coated so that they can have a good friction grip on the lineal L.

When roller 16a is depressed to engage the lineal L against drive roller 20a, the rotational speed of all the drive rollers 20a–20h is slowed. A motor controller (not shown) compensates by supplying more power to motor 24. This additional power quickly accelerates the lineal L to the desired velocity of two linear feet per second.

The present invention employs three imaging technologies to detect defects in the lineal L. The first of these technologies is high speed laser profiling, carried out by upper and lower high speed laser profiling systems 40 and 42, for gauging the thickness of the upper and lower lineal faces, respectively. Upper profiling system 40 includes a pair of side-by-side, 128×128 high speed black-and-white array cameras 44a and 44b; a pair of side-by-side cylindrical lenses 46a and 46b, placed in the optical paths of cameras 44a and 44b, respectively; a helium neon laser 50 that projects a pencil-shaped laser beam towards the upper lineal face, and a cylindrical lens 50a in the optical path of laser 50. An upper enclosure 52 houses cameras 44a and 44b, lenses 46a and 46b, laser 50; and lens 50a.

The black-and-white cameras 44a and 44b image the laser line appearing on the upper lineal face. Cylindrical lenses 46a and 46b are used to increase the thickness-sensing capability of the upper profiling system 40, while cylindrical lens 50a modifies the pencil beam of laser light into a fan beam of light that produces the laser line imaged where it intersects the lineal face. The lenses selected for all the cameras are ones that provide a cross-lineal imaging capability of 4 inches (1.016 centimeters).

Lower profiling system 42 is similar to upper profiling system 40, and comprises a pair of side-by-side, 128×128 high speed black-and-white array cameras 54a and 54b for imaging the laser line appearing on the lower lineal face; a pair of side-by-side cylindrical lenses 56a and 56b, placed in the optical paths of cameras 54a and 54b, respectively; a helium neon laser 60 that projects a pencil-shaped laser beam towards the upper lineal face; and a cylindrical lens 60a in the optical path of laser 60.

The laser lines projected by the laser and lens combinations 50 and 50a and 60 and 60a of both the upper and lower profiling systems 40 and 42 are parallel to one another and are both perpendicular to the direction of lineal travel.

The second of the imaging systems is x-ray imaging, carried out by the x-ray imaging system 70, for gauging the density of the lineal L. X-ray imaging system 70 comprises a conventional x-ray source 72, an x-ray collimator 74 immediately under the x-ray source 72, and a first enclosure 76 for housing x-ray source 72 and x-ray collimator 74.

Collimator 74 turns the cone shaped beam of x-rays produced by the source into a fan beam. The first enclosure 76 is lead lined to reduce the radiation emitted into the plant environment.

A vertically-extending second enclosure 80 is positioned immediately under enclosure 76 in alignment with collimator 74. The second enclosure 80 is also lead lined and envelops the fan beam from collimator 74 prior to its striking the lineal L. A horizontally-extending third enclosure 82 is provided under the second enclosure 80, and is tunnel-shaped to allow the lineal L to pass through it. Like the first and second enclosures 76 and 80, the third enclosure 82 is lead lined; it is designed to reduce the amount of scattered radiation that can emanate from the tunnel openings into the outside environment.

A vertically-extending fourth enclosure 84 is positioned immediately under the third enclosure 82, in alignment with the second enclosure 80, for enclosing the fan beam of x-rays transmitted through the lineal L. The fourth enclosure 84 is also lead lined. It encloses the fan beam of x-rays that were transmitted through the lineal L.

A conventional x-ray detector array 86 is positioned under the fourth enclosure 84, and is housed in a fifth lead-lined enclosure 88. The detector array 86 uses a scintillation material and photo diodes to sense the transmitted x-rays. The effective spatial resolution of the x-ray imaging system 70 is 32 pixels per inch.

The third and last of the imaging technologies is color imaging, carried out by upper and lower color imaging systems 90 and 92 for imaging the upper and lower lineal faces. Upper color imaging system 90 includes an upper color line scan camera 100 for imaging the upper lineal face and an angled sheet of metal 102 painted a special blue color and positioned in the optical path of the camera 100 to allow it to image blue pixels for all image points not on the upper lineal face. The color of blue chosen contains very little red or green. Hence the background pixels can easily be separated from pixels of a lineal face. First and second upper light sources, preferably tungsten halogen bulbs 104a and 104b, are provided to illuminate the upper lineal face, while a third upper light source, preferably a tungsten halogen bulb 104c, is provided to illuminate the metal sheet 102. Bulbs 104a–104c are enclosed in a separate upper bulb housing 106, to reduce the effects of the heat generated by the bulbs 104a–104c on the sensitive camera electronics.

First and second fiber optic light lines 112a and 112b are provided for carrying the light from the bulbs 104a, 104b to illuminate the upper lineal face, and a third fiber optic light line 112c is provided for carrying the light from bulb 104c, for illuminating metal sheet 102. This lighting arrangement allows the upper color camera 100 to image blue pixels for all image points not on the upper lineal face. The fiber optic light lines 112b, 112c and camera 100 are enclosed in an upper enclosure 114.

Lower color imaging system 92 is similar to upper color imaging system 90, and comprises a lower color line scan camera 120 for imaging the lower lineal face; an angled sheet of metal 122 painted the same special blue color as metal sheet 102; first and second tungsten halogen bulbs 124a and 124b used to illuminate the lower lineal face; a third halogen bulb 124c used to illuminate the metal sheet 122; a lower bulb housing 126 for enclosing bulbs 124a, 124b, and 124c; first and second fiber optic light lines 132a and 132b for carrying the light from first and second bulbs 124a, 124b, respectively, to illuminate the lower lineal face; a third fiber optic light line 132c for carrying the light from third bulb 124c, for illuminating metal sheet 122; and a lower enclosure 134 for housing camera 120 and fiber optic light lines 132a, 132b. The lighting arrangement for the lower color imaging system 92 allows the lower color camera 120 to image blue pixels for all image points not on the lower lineal face.

The imaging geometry and lenses used on cameras 100 and 120 are defined by compromising the need for adequate lighting, the need for a certain width of field of view, and the desire for generating images with a minimum of lens distortion. The embodiment of the invention described herein uses an effective spatial resolution of 64 color pixels per inch. Both of the camera enclosures 114 and 134 are air conditioned to maintain a consistent dark current of the cameras 100 and 120.

Enclosures 52 and 62 are attached to a metal support plate 140 that runs the length of the apparatus 10. Rollers 16a–16h and piston assembly 14 are also attached to this same support plate 140. The metal support plate 140 can be raised and lowered using conventional mechanical gearings (not shown) enclosed respectively in housings 142 and 144. The housings 142 and 144 are in turn respectively attached to metal supports 150 and 152. The gearings in housings 142 and 144 are powered by a motor or other conventional means that is not shown. Raising or lowering the support plate 140 allows lineals of different thicknesses to be inspected by the invention. Neither the position of the x-ray source 72 nor the position of the x-ray detector array 86 is changed by moving the support plate 140.

Figure 2B:
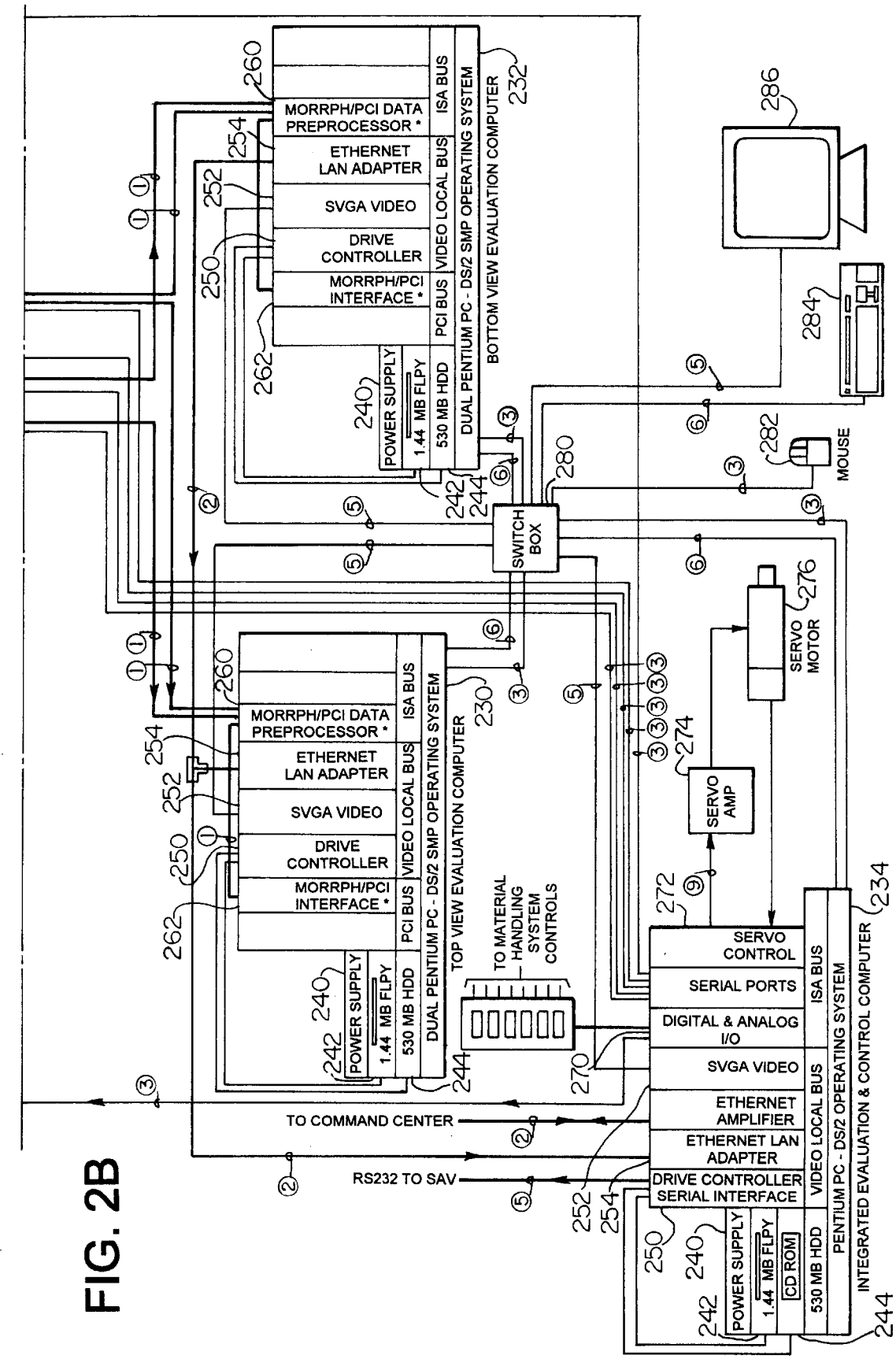
FIG. 2 is a block diagram illustrating the basic electronics components of the present invention and how these components are interconnected.

FIG. 2 shows the basic electronics components of the present invention and how these components are interconnected. The signal types, denoted by numerals in circles, are as indicated in Table 1.

TABLE 1

| Number | Signal Type |
| --- | --- |
| 1 | Pulnix bus |
| 2 | Ethernet LAN |
| 3 | Serial |
| 4 | Parallel |
| 5 | SVGA video |
| 6 | Keyboard |
| 7 | Analog voltage from color cameras |
| 8 | Differential pair digital |
| 9 | Analog voltage |

Components shown in FIG. 1 and also shown in FIG. 2 include the two 128×128 black-and-white cameras 44a and 44b and laser 50 used by the upper face laser profiling system 40; the 128×128 cameras 54a and 54b and laser 60 used by the lower face laser profiling system 42; the x-ray source 72 and x-ray detector 86 of the x-ray imaging system 70; the color camera 100 used to image the upper lineal face, the color camera 120 used to image the lower lineal face, and the light sources 104a and 104b and 124a and 124b used for illuminating both lineal faces in the upper and lower color imaging systems 90 and 92. FIG. 2 also shows a preamplifier board 200 needed to amplify the weak single created by the x-ray detector array 86; a power supply 202 for the lasers 50 and 60; and a DC power supply 204 for the light sources 104a–104c and 124a–124c.

As can be seen in FIG. 2, the analog signals from all the sensing systems 40, 42, 70, 90, and 92 are all directed to a VME based card cage 210 that contains the power supply 212 that powers all the sensors and their controllers; the two color camera controllers 214 and 216 that control each of the two color cameras 100 and 120 and that digitizes the analog output of each of cameras 100 and 120; the laser profiling system controller 220 that digitizes analog output of each of the 128×128 cameras 44a, 44b, 54a, and 54b, and that finds the laser line position in each column of black-and-white image; the x-ray controller 222 that digitizes the preamplified output of the x-ray detector array 86; and finally the multiplexer card 224 that multiplexes onto a single bus the digitized profiler data transmitted by laser profiling system controller 220 and the x-ray imagery transmitted by x-ray controller 222.

The information from the controllers 214, 216, 220, and 222 in the VME card cage 210 are variously sent to two different computers 230 and 232, each of which is identically configured and runs the same setup and analysis software. The role of these computers 230 and 232 is to process the multiple sensor imagery and to pass lineal feature locations, identities, and characteristics on to yet another computer 234 that is the integrated evaluation and control computer. Computer 230 is for processing the information obtained from the upper lineal face while computer 232 is for processing information obtained from the lower lineal face. This processing is done independently and in parallel by the two computers 230 and 232. The computers 230, 232, and 234 can be off-the-shelf microcomputers having, for example, dual Pentium® microprocessors and an OS/2 SMP operating system.

As shown in FIG. 2, each of the computers 230, 232, and 234 includes a power supply 240; a floppy disk drive 242 (for example, a 1.44 megabyte drive); a hard disk drive 244 for storing programs and data (for example, a 530 megabyte drive); and various cards that attach to each computer's PCI, ISA, and video local buses. These cards include an off-the-shelf hard drive controller card 250; an SVGA video card 252; and an ethernet card 254. The ethernet cards 254 of both computers 230 and 232 are used to transmit and receive information from the integrated evaluation and control computer 234 through the ethernet card 254 of the computer 234.

Each of the computers 230 and 232 also includes some special purpose image processing cards. These cards include a ISA based MORRPH/PCI data preprocessor card 260, that accepts information from the various sensors whose information the computer is to process. The MORRPH/PCI preprocessor card 260 is configured the same for both computers 230 and 232. The MORRPH/PCI preprocessor card 260 preferably is a reconfigurable pipelined processor that was developed at Virginia Tech and is currently sold by Pixell, Inc. Most of the image data preprocessing operations are performed by this card, thus enabling off-the-shelf microcomputers to be used to process multiple sensor information in real-time. The MORRPH/PCI preprocessor card 260 card in each of the computers 230 and 232 receives all the sensor information that is to be processed by the computer in which it resides.

Finally, each of the computers 230 and 232 includes an identically configured MORRPH/PCI interface 262. The purpose of the MORRPH/PCI card 262 is to transfer the image data from each of the sensor systems 40, 42, 70, 90, and 92 into computer memory in a standard direct memory access ("DMA") method so that no CPU intervention is required. The DMA method used is a PCI bus master interface. The PCI interface 262 preferably is a special purpose design that can accept up information from up to six different sensors, depositing the information from each in separate memory blocks.

The integrated evaluation and control computer 234 also includes a number of cards. The purpose of the computer 234 is to accept feature information about the upper lineal face from computer 230 and feature information about the lower board face from the computer 232 that is transmitted via ethernet. Once the computer 234 obtains this information it computes the best available sawing strategy for the lineal L based on the current cutting bill.

However, this is not the only responsibility of the computer 234. The computer 234 also controls all the materials handling components shown in FIG. 1. This is accomplished by using a digital and analog input/output (I/O) board 270. The computer 234 also controls the motor 24 that determines the speed at which lineals L will pass through the system. This is accomplished using the servo control 272, the servo amp 274, and the servo motor 276.

A manual switch box 280 is connected to all of computers 230, 232, and 234, which allows one mouse 282, one keyboard 284 and one monitor 286 to be I/O devices for any of the three computers 230, 232, or 234 described above.

Figure 3:
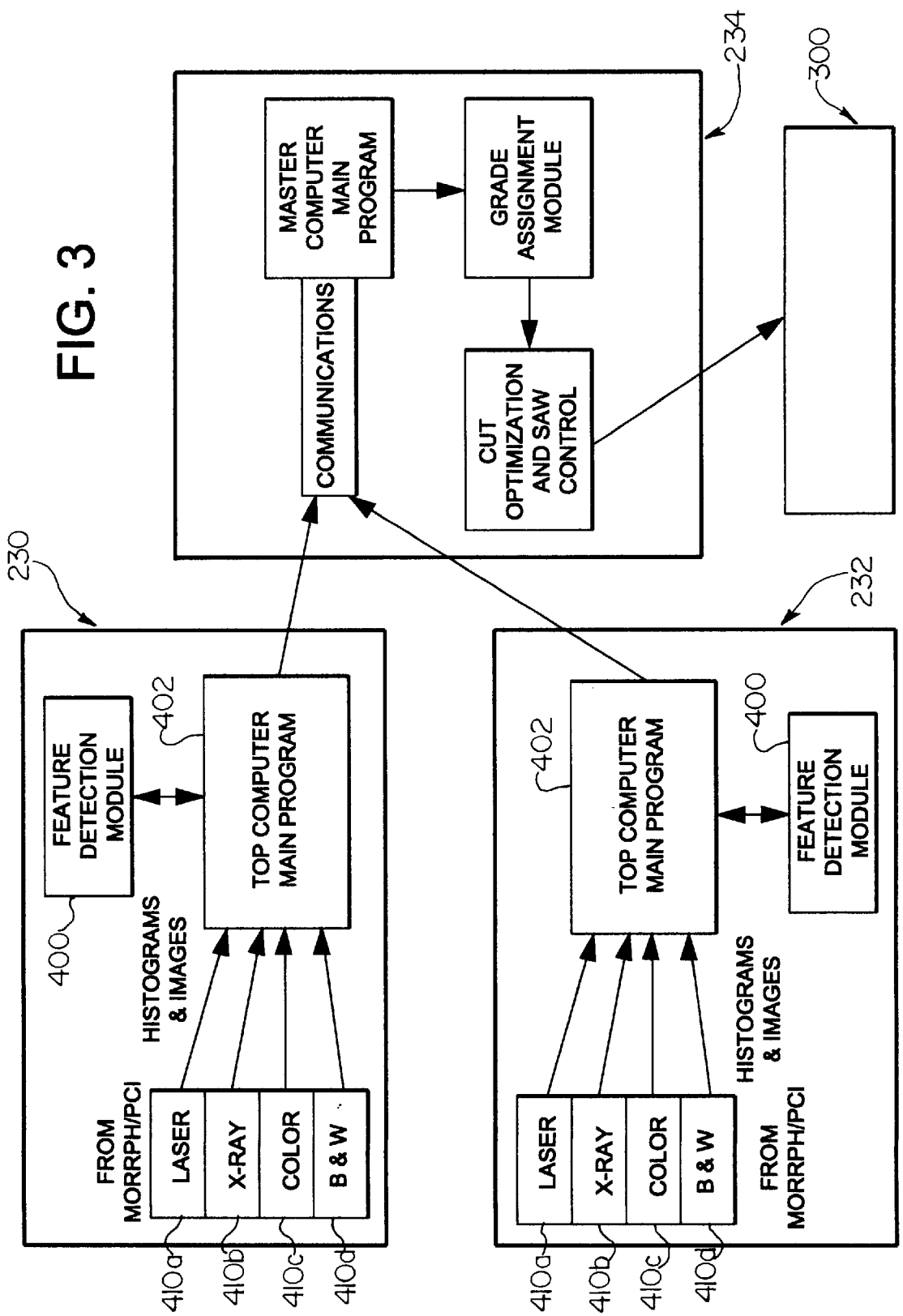
FIG. 3 is a block diagram illustrating the three computers of the present invention and the programming employed by the computers.

FIG. 3 provides an overview of the software used in this invention in conjunction with the apparatus. In the embodiment of the invention as shown in FIG. 3, all three computers 230, 232, and 234 run under a Windows NT operating system. As was stated above, the role of the integrated evaluation and control computer 234 is to formulate a sawing strategy based on the defects located by the two feature detecting computers 230 and 232. Once this strategy has been formulated, the integrated evaluation and control computer 234 passes control information on to a saw 300 which then performs the cutting.

Since the thrust of this invention is the defecting component of this automatic cross cutting system, the functioning of the integrated evaluation and control computer 234 will not be described in any degree of detail; nor will the nature of the communications that takes place between the feature detecting computers 230 and 232, and the integrated evaluation and control computer 234 be described in any degree of detail. It suffices to say that the information passed from the feature detecting computers 230 and 232 and the evaluation and control computer 234 includes coordinates that define a minimum inscribing rectangle of the lineal in the color image of the board, the board width in pixels again based on the color image data, the number of features found by the feature detecting computers 230 and 232, and for each feature found, a number that defines the identity of the feature and coordinates that define a minimum inscribing rectangle of the feature.

The image processing software that runs on the upper feature detecting computer 230 and the lower feature detecting computer 232 is identical. It is made up of two functional modules, a main program 400, and a feature detection module 402.

In this categorization of the software system, the role of the main program 400 on both computers 230 and 232 is to provide a user interface for performing such tasks as collecting the data needed to perform shading correction of the color and x-ray images, for calibrating the upper and lower laser profiling systems 40 and 42, i.e., for defining a mapping of pixel number to a physical dimension, etc. It is also responsible for handling all the communications that are needed between the feature detection computers, 230 and 232, and the integrated evaluation and control computer 234. At system startup, the main program 400 is responsible for loading programs into the field programmable gate arrays located on the MORRPH/PCI interfaces 262, the laser profiling board 220, the multiplexer board 224, and the color camera controllers 214 and 216. Finally, it is responsible for handling the interrupts generated by the MORRPH/PCI interfaces 262. This interrupt is generated after each MORRPH/PCI interface 262 has loaded all the image data collected from a lineal into the memory of its associated feature detection computer 230 or 232. As was stated above, this transfer is performed using a standard direct memory access method, and hence is completely transparent to the central processing units of the feature detection computers 230 and 232. Performing the transfer in this manner allows the feature detection computers 230 and 232 to be processing image data from one lineal while image data from the next lineal is being loaded into computer memory. This procedure markedly improves system throughput. Once the interrupt is generated, the main program 400 acknowledges the interrupt and then passes pointers to where each of the images are located to the feature detection software subsystem. There are separate pointers to each of the color channels, the derived black-and-white image, the x-ray image and the laser profile image.

While the main program 400 is somewhat logically complex, given the above-described functionality, one skilled in the art should be able to reconstruct this software system without the need of undue experimentation. Hence, this program will not be described in any further detail.

Image collection is performed by imaging modalities 410a–410d of computers 230 and 232 specifically, laser imaging modality 410a, x-ray imaging modality 410b, color imaging modality 410c, and black-and-white imaging modality 410d. All the imaging modalities 410a–410d are continuously collecting image data. As data is collected, each MORRPH/PCI interface 262 continuously examines the data stream from each imaging modality to determine when a lineal L has entered the field of view of a sensor. Only after the presence of a lineal L has been detected will image data from that sensing modality be transferred to the main memory of the affected feature detection computer 230 or 232. The MORRPH/PCI interface 262 can also detect when a lineal L has left the field of view of a sensor. This capability allows the MORRPH/PCI interface 262 to quit transmitting data to the feature detection computer immediately after a lineal has left the field of view of the sensor. It also allows the MORRPH/PCI interface 262 to interrupt the processor once all the data from all imaging modalities 410a–410d have been collected from the lineal L. This interrupt is then handled by the main program 400 in a manner described above. This capability markedly reduces the volume of data that must be collected and, hence, processed by the feature detection computers 230 and 232, thereby reducing the cost of this computer system. Further, as was stated above, this capability also allows the feature detection computers 230 and 232 to be processing data from one lineal while collecting image data from the next lineal.

Algorithms for detecting the presence of an object within the field of view of an imaging device are well known to those with skill in the art; hence, the precise method for performing this task will not be described in any detail except to say that an edge-based detection algorithm is used by the MORRPH/PCI interfaces 262.

The MORRPH/PCI interfaces 262 perform a number of other image processing functions in real-time as the data is collected. These rather computationally complex operations reduce the number of tasks that need to be performed by the feature detection computers 230 and 232, and make real-time operation of the system possible. The operations performed by the MORRPH/PCI interfaces 262 include (1) shade-correcting the color image data; (2) averaging the shade-corrected color image data to create a black-and-white image of the board; (3) shade-correcting the x-ray image data; (4) passing only image data collected from a specified field of view for each sensor to the affected feature detection computer 230 or 232 (5) appending to each line of image data collected from each sensor the two column numbers that specify where the lineal L is within the field of view; (6) reducing the resolution of the color image data from 64 pixels per inch cross board and 32 pixels per inch down board to 32 pixels per inch cross board by 16 pixels per inch cross board using a crack-preserving filter; (7) generating histograms of pixels of the lineal L from the red color channel, green color channel, blue color channel, the computed black-and-white image, and the x-ray image; and (8) segmenting the laser profile image into three categories, i.e., unknown, too thin, and thick enough. This segmented laser image is placed in computer memory in the manner described above for the other image data.

Methods for shade-correcting image data, generating a black-and-white image by averaging the color channels of a color image, finding edge points of objects within a field of view, selecting a field of view, and generating histograms of images are all known by those skilled in the art and, hence, will not be described here.

As for the crack-preserving filter, cracks are the smallest features the feature detection system of the present invention must be able to locate. Detecting cracks therefore drives the selection of imaging system resolution. Unfortunately, all the spatial resolution needed to find cracks is wasted on the other features the system must find. Hence, to reduce the volume of data that must be collected and processed by the system a crack-preserving filter is employed. Let R(i, j) be the red channel of a color image, let G(i, j) be the green channel, and let B(i, j) be the blue channel. Suppose that both i and j are even numbers. The crack-preserving filter examines the pixels with locations (i, j), (i+1, j), (i, j+1) and (i+1, j+1). Let (k, l) be the location in this set of four locations that minimizes $$\frac{R+G+B}{3}.$$

Then the reduced resolution color image, $R_r(i, j)$, $G_r(i, j)$, and $B_r(i, j)$, produced by the crack-preserving filter is defined by:

$$R_r(i/2, j/2) = R(k, l)$$

$$G_r(i/2, j/2) = G(k, l)$$

$$B_r(i/2, j/2) = B(k, l)$$

As to segmenting the laser image, a fixed threshold is used to differentiate pixels that are classified as thick enough from those that are classified as too thin. A pixel in the laser image is labelled as unknown in the segmented image if it has a gray level value of 255. Two different situations give rise to unknown pixels in the segmented image. One possibility is when the line of laser light is not within the field of view of any of the cameras 44a, 44b or 54a, 54b of the laser profiling systems 40 and 42. This is the situation when there is no lineal L in the field of view of the laser profiling cameras 44a, 44b, 54a, and 54b. A second situation that will cause an unknown pixel to be generated is when the lineal surface is very dark, so dark that the laser line cannot be detected by the laser profiling cameras 44a, 44b, 54a, and 54b. Both cases result from the fact that if the upper and lower laser profiling systems 40 and 42 cannot find the laser line in a column of data it, always assigns the last element of the column as being the location of the line.

Figure 4:
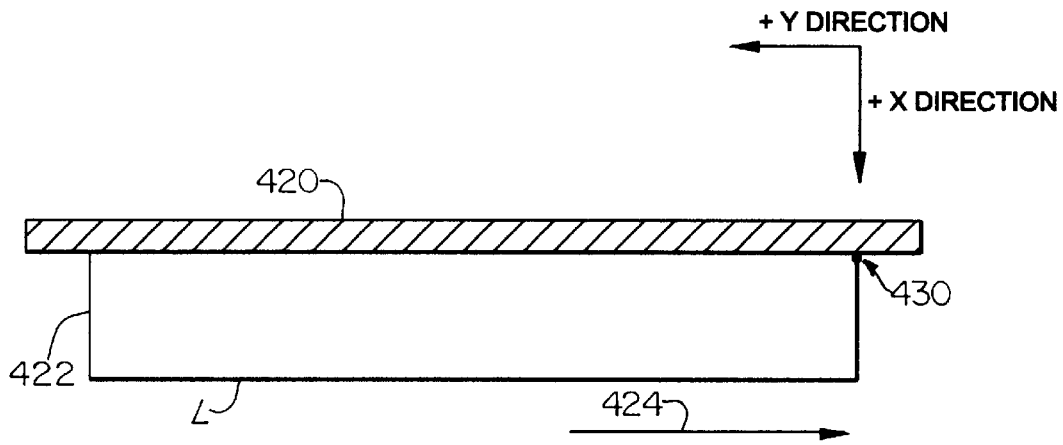
FIG. 4 is a diagrammatic view illustrating a lineal supported on a fixed mechanical fence of a materials handling system incorporated in the apparatus of FIG. 1, and the common coordinate system employed by the present invention relative to the position of the lineal.

As with most multiple sensor systems, the problem of image registration must be addressed. One of the problems involves establishing a common coordinate system among the various sensing technologies. FIG. 4 shows the common coordinate system employed in this invention. The apparatus 10 illustrated in FIG. 1 includes a materials handling system (not shown in FIG. 1). As shown in FIG. 4, this materials handling system includes a fixed mechanical fence 420. An objective in the design of the materials handling system is to keep one of the long lineal edges 422 tight against this fence 420. Note that lineals should contain very little wane and the majority of both long edges of the lineal should be straight. This fact reduces the complexity of the above-described positioning problem. However, there is always the possibility of some drift away from the fence 420 as the part goes through the apparatus 10. The feature detection software must be able to tolerate some acceptable level of lineal drift as it performs its analysis.

The direction of lineal travel through the apparatus 10 is indicated by the arrow 424. For purposes of this invention it is assumed that the materials handling system will be able to move the lineal L through the imaging components at a constant velocity along the direction of travel 422, which is the same as the imaging axis. Making this assumption reduces the computational complexity of the analysis problem by not having to address part drift along this imaging axis. The methods which will be described later for coping with part drift away from the fence 420 can easily be generalized to also handle part drift along the direction of travel should the need arise.

The common coordinate system is defined by the x- and y-axes illustrated in FIG. 4. The origin of this system on each image collected is assumed to be at point 430. The starting x-coordinate is always located immediately adjacent to the fence 420. The starting y-coordinate of each image is the first line of image data where the lineal L appears. The MORRPH/PCI interface 262 starts the collection of image data at precisely the moment it detects that a lineal L is in the field of view of one of the imaging modalities, i.e., systems 40, 42, 70, 90, and 92. This coordinate system is used on all the imaging modalities, including the color image collected by the lower color camera 120.

To select the appropriate x-coordinate in the original image data that will be assigned the value 0 in the new coordinate system can be determined by routine experimentation in a manner well known by those of skill in the art. Once this coordinate is selected, it is used as one of the points defining the field of view for a sensor. The other coordinate defining the field of view is based on the widest part the apparatus 10 is expected to handle for a particular application.

A second item of concern in addressing the registration issue, is the spatial resolution of each sensing modality. Theoretically, registered images can be obtained by mathematical transform from sensors with any known spatial resolution. However, these transformations require a good deal of floating point processing. To reduce computational complexity and hence reduce computer cost, this transformation must trivialized. Practically speaking, this means that either all the sensors should have the same spatial resolution or should have spatial resolutions that differ by a power of two. This invention uses sensors that all have the same special resolutions, 32 pixels per inch down lineal resolution and 16 points per inch cross lineal resolution. The color image data is collected at a higher resolution than this, but then is mapped down to this resolution using the crack-preserving filter.

The feature detection software of this embodiment of the invention is able to recognize a number of classes of features in wood. One rather broad class of features is called knots. However, this feature class includes not only knots but other similar features such as burl, bud trace, and bird peck as well. Whenever one of these features occurs on a lineal surface it will be assigned the knot label. To be assigned this class label, an area must not only be of higher density than clear wood, but also it must possess some surface discoloration.

A second feature class called scant. An area of a lineal is considered to be scant if it is too thin to be made into a finished part. Scant areas on a lineal could be areas of wane, large holes, saw marks, and the like. Whatever the cause, the feature detection software assigns such areas the class label scant.

The third feature class is called decay. If white rot, brown rot, and maybe bark pockets occur on a lineal surface the feature detection software will assigns these areas the class label of decay. As in the case with class knot, an area must not only be less dense than clear wood but also it must have some surface discoloration.

A fourth class is called mineral streak. An area of a lineal surface will be assigned the label mineral streak if the mineral streak is visible on the surface of the lineal.

The fifth feature class is called crack. The crack class includes splits and checks that are visible on the lineal surface.

The sixth feature class is called high density area. An area is assigned the label high density area if it is more dense than clear wood and has no associated surface discoloration.

The seventh feature class is called low density area. Like the high density area class, an area will be labeled low density area if the area is less dense than clear wood and has no associated surface discoloration.

The eighth feature class is called hole. Any rather small scant area of a lineal will be assigned this class label. As with some of the above classes, for an area to be assigned the hole class it must be scant, less dense that clear wood, and have some detectable surface discoloration.

The ninth feature class is called surface stain. An area of a lineal will be assigned this class label if it has a color different from clear wood while not affecting the detectable structure of the underlying wood, i.e., wood density.

The last feature class is crayon mark. An area of a lineal will be assigned this class label if it has been marked with a crayon of a particular color. This class was added so that manual marking of special features can be employed to address a particular application. This manual marking capability allows the system to be applied to a variety of special purpose applications.

The feature detection software 402 shown in FIG. 3, running on the upper feature detecting computer 230, has access only to the MORRPH/PCI-generated color imagery, black-and-white imagery, laser profile imagery of the upper lineal face, and the x-ray image of the lineal supplied by the MORRPH/PCI. Hence, this software is only capable of labeling areas as knot, decay, mineral streak, crack, hole, surface stain, or crayon mark if they have discolorations on the upper surface of the lineal. Similarly, the feature detection software 402 shown in FIG. 3, running of the lower feature detecting computer 232, has access only to the color imagery, black-and-white imagery, laser profile imagery of the lower lineal face, and the x-ray image of the lineal supplied by the MORRPH/PCI. Therefore just as was the case previously, this software is only capable of labeling areas as knot, decay, mineral streak, crack, hole, surface stain, or crayon mark if these areas have discolorations on the lower surface of the lineal.

Because of the above, the integrated evaluation and control computer 234 must identify features that are completely internal within a lineal L. Completely internal features are those features that are not visible on either surface of the lineal L. To locate such features, the integrated evaluation and control computer 234 must look for and identify areas that have been labeled as low density or high density by both the upper and lower image processing computers 230 and 232.

The feature detection software 402 is composed of three modules. These modules include a module for processing the laser image, a module for processing the x-ray image, and finally a module for processing the color image. Note the while there is one module for processing each of the sensed images, the processing of each image is not done independently, correlations are performed across imaging modalities to improve the accuracy of both the detection and labeling of features.

The algorithms employed were formulated by the present inventors to improve the invention's ability to detect small features, to minimize the computational complexity of the analysis tasks, and to fully utilize the information contained in each imaging modality.

The laser image processing module receives as input the laser image, edge information about where the lineal L is located in the laser image, and a thickness threshold. The laser image is passed to this module via a pointer. The edge information is appended to each row of the laser image. For a particular row, the information provided is the starting column location of the lineal L in this row and the ending column location of the lineal L in this row. This information is generated via the MORRPH/PCI interface 262. The thickness threshold is used to define when an area is too thin.

The module uses the thickness threshold to segment that part of the laser image that lies between the starting and ending column locations for each row. The segmentation involves a pixel-by-pixel labeling into one of the three above-described classes thick enough, too thin, and unknown. The thick enough and too thin labeling is based on the thickness threshold. As was discussed above, pixels are assigned to the unknown class if it is either from an area that is very thin or from and area of the lineal's surface that is very dark, so dark that the presence of the laser line on the cameras 44a, 44b, 54a, and 54b cannot be detected by the upper and lower laser profiling systems 40 and 42. A pixel is assigned to the unknown class if it equals a value N where N is equal to the number of elements in each row of the array cameras 44a, 44b, 54a, and 54b used by the laser profiling systems 40 and 42. The output of this segmentation operation is called the segmented laser image.

Once the segmented laser image is found, a connected component labeling algorithm is applied to this image. This algorithm looks for four-neighbor connectedness. The goal of this operation is to find connected regions where all the pixels within the region have either the too thin or unknown class label. The output of this operation includes: 1) an image, called the connected component labeled laser image; 2) a region property table that gives the minimum inscribing rectangle of each connected region, the area of each connected region, and the percent of each region's boundary that touches the background, i.e., that part of the image that is not of the lineal L; and 3) a number that specifies the total number of connected regions that have been found. In the connected component labeled image, each pixel in the $m^{th}$ region found is assigned gray level m. The region property table is called undetermined_laser.

Based on the region characteristics appearing in undetermined_laser, regions are either removed from consideration or assigned to the feature class scant. A region is removed from consideration if its area is smaller than a user-defined threshold, $T_{small\_laser}$. When a region is removed, its entry in the undetermined_laser table is erased and its pixels in the connected component labeled image are assigned the gray level value used to indicate thick enough. A region is assigned to the scant feature class, if all the pixels in the region are too thin and if the region's area is larger than some user defined threshold $T_{large\_laser}$. Finally even though a region may have an area smaller than $T_{large\_laser}$ it can still be assigned to the scant class if the percentage of its boundary that touches the background is larger that the user defined threshold $T_{boundary}$. This last test labels small areas of wane along the edge of the lineal L. Regions that are given a feature class label are moved from the undetermined_laser table to the feature table. Once all the connected regions appearing in undetermined_laser have been examined, the processing in this module terminates.

The module for processing the x-ray image is initiated next. Its inputs are:
1. The x-ray image of the lineal L with the edge points of the lineal appended to each row,
2. A histogram of those pixels in the x-ray image that are of the lineal L,
3. The segmented laser image,
4. The connected component labeled laser image,
5. The undetermined_laser table,
6. The feature table,
7. The color image with lineal edge points appended to each row,
8. The derived black-and-white image with the lineal edge points appended to each row,
9. The red, green, and blue histograms of pixels in the color image that are of the lineal L, and
10. The histogram of pixels in the derived black-and-white image that are of the lineal L.

Upon entering this module, the elements of the feature table are examined. If a labeled region appearing in this table is larger than a specified size, its minimum inscribing rectangle is used to remove the effects of this feature from all the input histograms. Removing the effects of these larger features from the histograms aids in locating and identifying smaller features on or within the lineal L.

The process of removing the effects of the larger features begins with all of the histograms being smoothed using a Gaussian filter. The size of filters used is sensor-dependent and is determined by routine experimentation in a conventional manner known to those of skill in the art. After smoothing, the highest peaks in the smoothed red, green, and blue histograms are found. The position of the highest peak in the red channel is called $Av_{red}$, the position of the highest peak in the green channel is called $Av_{green}$, and the position of the highest peak in the blue channel is called $Av_{blue}$. The highest peak in the smoothed histogram of the x-ray image is also found and is called $Av_{x\text{-}ray}$.

The underlying assumption upon which many of the processing algorithms employed in this invention are based is that most of the lineal L will be clear wood. Hence the largest peak in the histogram of any image will be from pixels of clear wood. In the above instance, this assumption means that ($Av_{red}$, $Av_{green}$, $Av_{blue}$) is a good estimate for the average color of the clear wood part of the lineal L. Similarly, it implies that $Av_{x\text{-}ray}$ should be a good estimate of the average gray level value of clear wood in the x-ray imagery.

Figure 5:
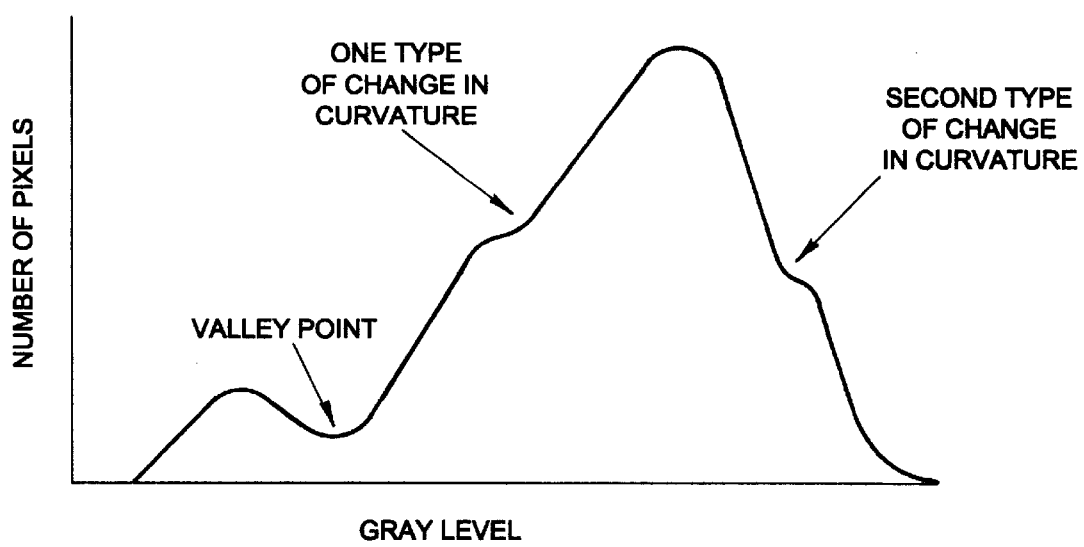
FIG. 5 is a smoothed histogram of x-ray image data, showing the location of the highest (i.e., the clear wood) peak, the location of valley points, and the location of points that represent changes of curvature.

The smoothed histogram of the x-ray image data is then processed to find the location of the highest peak, i.e., the clear wood peak, the location of any valley points, and the location of points that represent changes of curvature in the histogram of the type shown in FIG. 5. It is assumed that any such point is caused by a mixing of populations with different distributions, i.e., the mixing of a distribution caused by the presence of a feature with that of the distribution of clear wood. Algorithms for finding such points abound in the image processing literature and, hence, are well known to those skilled in the art.

Using the locations of these points, two thresholds, $T_{low}$ and $T_{high}$, are automatically selected. Some of the rules for selecting the thresholds are as follows:

1. If there are no valley points or there are no changes of curvature of the type shown in FIG. 5, then set $T_{low}=0$ and $T_{high}=255$. This condition occurs when the lineal L is completely clear of features.

2. If there is a valley point whose location is to the left of the highest peak top and there are no changes of curvature of the type shown in FIG. 5, then $T_{low}$ is set equal to the position of the valley point and $T_{high}=255$.

3. If there is a valley point whose location is to the left of the highest peak top and there is a change of curvature also to the left of the highest peak but not to the right of the valley point, then $T_{low}$ is set equal to the location of the change of curvature and $T_{high}=255$.

4. If there is a valley point whose location is to the right of the highest peak top and there is no change of curvature of the type shown in FIG. 5, then $T_{low}=0$ and $T_{high}$ is set equal to the location of the valley point.

The above represent a sampling of the rules used and do not represent an exhaustive list. The set of rules used in this invention exhaust all possible combinations of valley points and changes in curvature in the x-ray histogram. The goal is to find two dynamic thresholds, one that defines the separation between pixels that are as dense as clear wood and those that are less dense. The second threshold is used to separate pixels that are as dense as clear wood from those that are denser than clear wood. Based on this objective, those skilled in the art can easily formulate the exhaustive list without undue experimentation.

After the thresholds have been selected, the pixels in the x-ray image that are of the lineal L are segmented into three classes, lower density, higher density, and clear wood density. The output of this operation is called the segmented x-ray image.

Once the segmented x-ray image is found, a connected component labeling algorithm is applied to this image. The algorithm used is the same as that which is used on the segmented laser image. The goal of this operation is to find connected regions where all the pixels within a region have either the lower density or higher density class label. The output of this operation is 1) an image, called the connected component labeled image; 2) a region property table that gives the minimum inscribing rectangle of each connected region, the area of each connected region, the average x-ray gray level of the pixels within each connected region, the height/width ratio of each connected region, and the compactness of each connected region; and 3) a number that specifies the total number of connected regions that have been found. The height of a region is measured along the lineal L. The width of a region is measured across the lineal L. The compactness of a region is the ratio of its area to the area of its minimum inscribing rectangle. Compactness is a measure of the fullness or roundness of an object. As was the case in the processing of the laser data, in the connected component labeled x-ray image, each pixel in the $m^{th}$ region found is assigned gray level m. The region property table is called undetermined_x-ray.

Based on the region characteristics appearing in undetermined_x-ray, regions are either removed from consideration or an attempt is made to assign a feature class to the region. A region is removed from consideration if its area is smaller than some user defined threshold, $T_{small\_x-ray}$. When a region is removed, its entry in the undetermined_x-ray table is erased and its pixels in the connected component labeled x-ray image are assigned the gray level value used to indicate clear wood density.

Because of the way the feature classes are defined, to assign a class label to a region in the x-ray image requires that the attributes of the corresponding regions in the color and laser images be examined. Hence, image registration becomes important at this stage of the processing. As was mentioned previously, it is assumed that the images from all three imaging modalities are perfectly registered in the lengthwise lineal direction but that potential registration problems can occur in the crosswise lineal direction because of lineal wander away from the fence. Therefore, the analysis algorithms must address this problem.

Because the methods for coping with registration problems are relatively computationally complex, two approaches are employed. First, if the region is appropriately large and has a large enough width, then correlation errors caused by cross-board registration errors should not markedly affect values of the measures computed from exact corresponding regions in the other imaging modalities. By exact correspondence is meant that if pixel (i, j) is the one of interest in the x-ray image, then its exact corresponding point in both the color image and the laser image is also (i, j). Therefore, the first regions to be examined are the ones that have appropriately large area and appropriately large width.

To begin the process of class assignment, a region is selected from the undetermined_x-ray table that is appropriately large and appropriately wide. The average color, i.e., average red ($A_{red}$), average green ($A_{green}$), and average blue ($A_{blue}$) components, is computed from the exact corresponding region in the color imagery. Also, the exact corresponding region in the segmented laser image is examined. This examination involves computing the percentages of the number of pixels in the exact corresponding region that are too thin, unknown, and thick enough. Let Percent(too thin), Percent(unknown), and Percent(thick enough) denote each of these percentages, respectively.

Based on the values of $A_{red}$, $A_{green}$, and $A_{blue}$, some additional measurements are computed, measurements that make certain aspects of the color properties of the exact corresponding region in the color image explicit. First the vector ($A_{red}-Av_{red}$, $A_{green}-Av_{green}$, $A_{blue}-Av_{blue}$) is computed, where ($Av_{red}$, $Av_{green}$, $Av_{blue}$) is an estimate of the average color of clear wood that was computed previously. Call ($A_{red}-Av_{red}$, $A_{green}-Av_{green}$, $A_{blue}-Av_{blue}$) the relative_color_vector for the region.

By taking the dot product of the relative_color_vector with the vector ($1/\sqrt{2}$, $1/\sqrt{2}$, $1/\sqrt{2}$), i.e., the vector that defines the black/white line in color space, one gets a scalar that indicates whether the region is darker than clear wood (negative dot product) or brighter than clear wood (positive dot product). Call this dot product relative_intensity. Also, the magnitude of the scalar indicates how much darker or lighter the region is than clear wood; and by computing the orthogonal projection of relative_color_vector onto the plane defined by $\vec{w}\cdot\vec{x}=0$, where $\vec{w}=(1/\sqrt{2}, 1/\sqrt{2}, 1/\sqrt{2})$, one can determine whether the region is redder, greener, bluer, etc., than clear wood. Call this orthogonal projection $\vec{o}$. Then, for example, to determine whether the region is redder than clear wood, one need only take the dot product of the vector $\vec{o}$ with the vector (1, 0, 0) that defines the red axis of color space. A positive dot product means that the region is redder than clear wood and, in this case, the magnitude of the dot product indicates how much redder it is.

Figure 6:
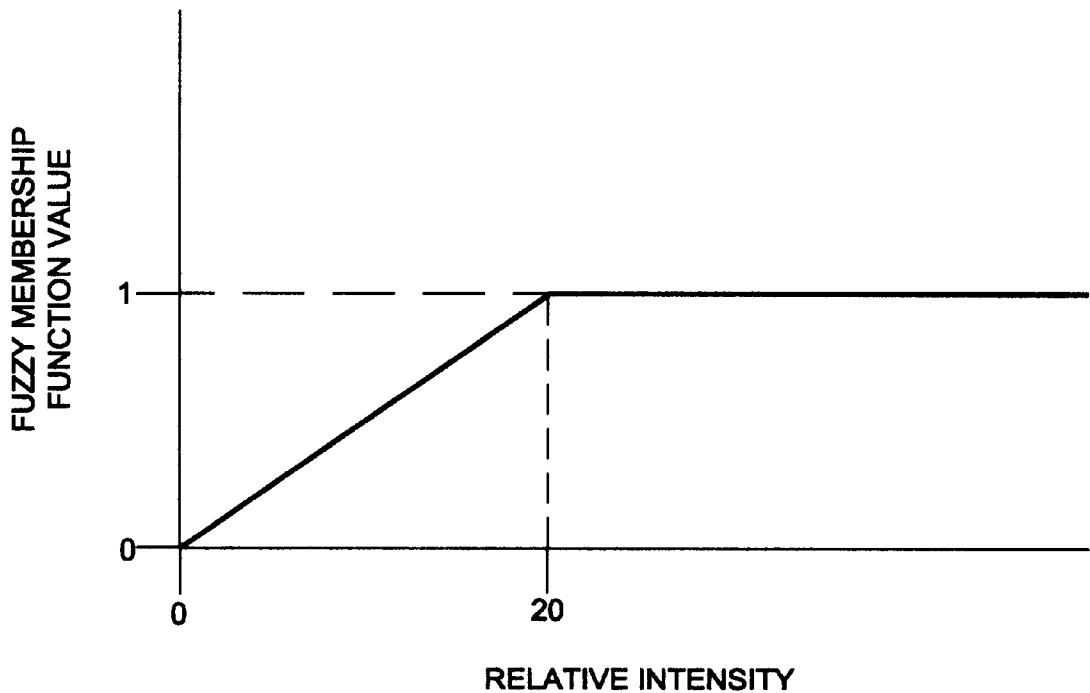
FIG. 6 is a graph illustrating a fuzzy membership function for the set defined by the fuzzy concept "lighter than clear wood."

All of the above-described measures form the basis for an inexact descriptive vocabulary that will be used to classify features. Each measure defines a descriptive adjective, the conjunctions and disjunctions of which are used as the descriptions for the features. These adjectives take the form of darker, lighter, redder, bigger, rounder, etc. Since the concepts of darker than, redder than, larger than, rounder than are not crisp concepts but fuzzy ones, fuzzy logic is used in making the decisions. The fuzzy membership functions used to define memberships in the fuzzy sets will be piece-wise linear, i.e., of the form shown in FIG. 6. The example shown in FIG. 6 is a fuzzy membership function for the set defined by the fuzzy concept "lighter than clear wood." As will be noted, regions being only a few gray levels brighter than clear wood do not have high membership function values, while ones that differ by a number of gray levels do have high membership function values. The definition of these functions must be done through routine experimentation in a manner known to those of skill in the art, and in many cases will probably be application-dependent. This invention uses standard methods for assigning membership function values to conjunctions, disjunctions, and complements of the basic set of adjectives, i.e., the maximum of the membership functions for the OR-ing of two sets, the minimum of the membership function values for the AND-ing of two sets, and one minus the membership function values for the negation of complement of a set.

Some of the rules used to make feature classifications in this embodiment of the invention are presented below:

{[If a region is denser than clear wood (fuzzy membership function based on the difference between $Av_{x-ray}$ and the average gray level of the region in the x-ray imagery), and if it is darker than clear wood (fuzzy membership function based on relative_intensity), and if it is redder than clear wood (fuzzy membership function based on $\vec{o}$ dotted with (1, 0, 0)), and if the region is round (fuzzy membership function based on compactness AND-ed with fuzzy membership function based on height/width ratio), and if the region is flat (fuzzy membership function based on Percent(too thin)), then the region is a knot.]

OR

[If a region is denser than clear wood (fuzzy membership function based on the difference between $Av_{x-ray}$ and the average gray level of the region in the x-ray imagery), and if it is darker than clear wood (fuzzy membership function based on relative_intensity), and if it is redder than clear wood (fuzzy membership function based on $\vec{o}$ dotted with (1, 0, 0)), and if the region is round (fuzzy membership function based on compactness AND-ed with fuzzy membership function based on height/width ratio), and if the region is has some small cracks (fuzzy membership function based on Percent(too thin)), then the region is a knot.]}

OR
[If a region is less dense than clear wood (fuzzy membership function based on the difference between $Av_{x\text{-}ray}$ and the average gray level of the region in the x-ray imagery), and if it is darker than clear wood (fuzzy membership function based on relative_intensity), and if it is grayer than clear wood (fuzzy membership function based on the magnitude of the vector that is the orthogonal projection of $(A_{red}, A_{green}, A_{blue})$ onto the plane defined by $\vec{w}\,\vec{x}=0$, where $\vec{w}=(1/\sqrt{2}, 1/\sqrt{2}, 1/\sqrt{2})$), and if some of the region is not thick enough (fuzzy membership function based on Percent(too thin) OR-ed with fuzzy membership function based on Percent(unknown)), then the region is a hole.]

OR
[If a region is denser than clear wood (fuzzy membership function based on the difference between $Av_{x\text{-}ray}$ and the average gray level of the region in the x-ray imagery), and if it is darker than clear wood (fuzzy membership function based on relative_intensity), and if it is redder than clear wood (fuzzy membership function based $\vec{0}$ dotted with (1, 0, 0)), and if the region is elongated (fuzzy membership function based on compactness AND-ed with fuzzy membership function based on height/width ratio), and if the region is flat (fuzzy membership function based on Percent(too thin)), then the region is a mineral streak.]

OR
[If a region is less dense than clear wood (fuzzy membership function based on the difference between $Av_{x\text{-}ray}$ and the average gray level of the region in the x-ray imagery), and if it has the same color as clear wood (fuzzy membership function based on the magnitude of the relative_color_vector), and if the some of the region is thick enough (fuzzy membership function based on Percent(too thin)), then the region is a low density region.]

OR
[If a region is more dense than clear wood (fuzzy membership function based on the difference between $Av_{x\text{-}ray}$ and the average gray level of the region in the x-ray imagery), and if it has the same color as clear wood (fuzzy membership function based on the magnitude of the relative_color_vector), and if the some of the region is thick enough (fuzzy membership function based on Percent(too thin)), then the region is a high density region.]

The above rules do not represent the totality of those used in the invention. However, generating a complete list of rules that will address a particular application can be done by one skilled in the art through routine experimentation.

The result of applying each rule is a value for a fuzzy membership function whose fuzzy set is defined by the terminology of the rule. The region is placed in the class whose rule generates the largest fuzzy membership function if, in addition, this fuzzy membership function has a sufficiently high value. In instances when two or more class fuzzy membership functions have sufficiently high but equal values, the feature is placed in the worst possible class, i.e., the one that will assure it is removed in the saw-up. If none of the class fuzzy membership functions are sufficiently large, the region and its attributes are placed in the undetermined_x-ray table.

After a region is labeled, an analysis is performed to determine whether it contains or shares a high percentage of the same area as regions in the undetermined_laser table. If it does contain or shares a high percentage of same area with any region in the table, it is removed from the table and the gray level of this region's pixels in the connected component labeled laser image are changed to the gray level used to denote thick enough.

Recall that only those regions of sufficient size and of sufficient width are labeled in the processing described above. Because these regions are by definition large ones, their presence on the board surface may conceal the effects of small defects on all the histograms, thus making the task of locating these defects either difficult or impossible. To aid in the detection of small defects as each region is labeled, the histogram of x-ray pixels in the region's minimum inscribing rectangle is subtracted from the x-ray histogram. Similarly, the histogram of the pixels in the exact corresponding minimum inscribing rectangle in the color image is computed and subtracted from the histograms of the red, green, and blue channel histograms and the derived black-and-white histogram, thereby removing the effects of these large features from these histograms.

After all of the regions have been labeled and had their effects removed from all the histograms, these histograms are once again smoothed using a Gaussian filter. After smoothing, the same techniques as described above are applied to the histogram of the pixels in the x-ray image that are of the lineal L. Using these methods, new values for $T_{low}$ and $T_{high}$ are computed using the same exhaustive set of rule alluded to above. These thresholds are used to perform another segmentation. This segmentation uses the same algorithms as described above. However, this segmentation does not involve those areas of the image that have already been labeled. Then another connected component labeling operation is performed yielding a new undetermined_x-ray table. Again the connected component labeling does not involve those areas of lineal L that have already been labeled. This table has the same form as the one described previously. After the table is created, the labeling operation is performed again using the same rules as alluded to above.

All the processing proceeds exactly as above but for one notable exception. This exception involves the way the images are registered so that information can be collected across imaging modalities. On this round of processing, the regions are smaller than before. Therefore, using exact corresponding pixels in each image will not yield good results. To accomplish the registration, a correlation is performed to assure proper correspondence. The template used is a binary image of the same size as the region's minimum inscribing rectangle. It is created by assigning every pixel point in the minimum inscribing rectangle that is not in the region, a value of zero in the binary template, and assigning every pixel that is in the inscribing rectangle and in the region, a value of one in the binary template.

Once the template is created, it is matched with the image data from the other modality along the cross-board direction. The matching is the standard template matching operation used in image processing. Depending on the type of information the program is attempting to obtain, it will look for a maximum or a minimum output of the matching operation. Whichever extreme is located, the position that is found provides an offset that is used in registering the data from the two imaging modalities for this region of interest. Clearly, this technique can be generalized in a straightforward manner to handle the situation where there can be drift in both the lengthwise and crosswise lineal directions.

After all the above-described processing has been completed, undetermined_x-ray should be empty, with all the connected components found during the connected component labeling operation having been assigned to a feature class or to the clear wood class.

Once the processing of the x-ray image is complete, the color image processing module is initiated. This module is responsible for analyzing that part of the color image where features have not already been found by either the analysis of the laser imagery or the analysis of the x-ray imagery. For any particular feature that has been found, its minimum inscribing rectangle is removed from consideration in the analysis of the color image data.

Because of the way the processing is structured, the only types of features that should remain to be found in the color image data are small cracks, surface stains, and crayon marks. Hence, this module is designed to recognize only these three feature classes. It is noted that because of the above-described crack preserving filter the color imagery can be used to find cracks much smaller than can be found in the other imaging modalities. The analysis of the color image is performed last because the analysis of this data is the most ambiguous, i.e., two different wood features can have exactly the same color.

The inputs into the module for processing the color image include:
1. The segmented laser image,
2. The connected component labeled laser image,
3. The color image with lineal edge points appended to each row,
4. The derived black-and-white image with the lineal edge points appended to each row,
5. The feature table,
6. The vector ($Av_{red}$, $Av_{green}$, $Av_{blue}$),
7. The histogram of the black-and-white image that are of the lineal but which has been updated to remove the effects of pixels that lie in any of the minimum inscribing rectangles associated with the features that have already been found.

Upon entering this module, the elements of the feature table are examined. If a labeled region appearing in this table is smaller than the specified size used to separate large from small areas in the processing of the x-ray imagery, its minimum inscribing rectangle is used to remove the effects of this feature from the black-and-white input histogram. The effects of the large features have already been removed from this histogram in the processing described above. Removing the effects of these features from this histogram aids in locating and identifying small cracks and light stains on the surface of the lineal.

Next, the black-and-white histogram is smoothed using a Gaussian filter. This smoothed histogram is then processed to find the location of the highest peak, i.e., the clear wood peak, the location of any valley points, and the location of points that represent changes of curvature in the histogram. This algorithm is exactly the same as the one described above for segmenting x-ray imagery. Using these locations of the points, two thresholds, $T_{low}$ and $T_{high}$, are automatically selected. Rules are employed for selecting the thresholds. The same rules as described above for x-ray imagery are used for selecting these thresholds.

After the thresholds have been selected, the pixels in the black-and-white image that are of the lineal and not of any of the previously-found features are segmented into three classes, brighter intensity, darker intensity, and clear wood intensity. The output of this operation is called the segmented color image. The underlying assumption used in this analysis is that features in wood affect the black-and-white intensity of the wood as well as the hue and saturation of the color. Hence, using the black-and-white imagery to do the segmentation is computationally the simplest approach to use. Because the black-and-white image is derived from the color imagery, both are perfectly registered. Hence, regions or connected components found in one image exactly correspond to the same area of the other image.

Once the segmented color image is found, a connected component labeling algorithm is applied to this image. The algorithm used is the same as is used on the segmented laser image and the segmented x-ray image. The goal of this operation is to find connected regions where all the pixels within a region have either the brighter intensity or darker intensity class label. The output of this operation is (1) an image, called the connected component labeled color image; (2) a region property table that gives the minimum inscribing rectangle of each connected region, the area of each connected region, the average color ($A_{red}$, $A_{green}$, $A_{blue}$) of the pixels within each connected region, the height/width ratio of each connected region, and the compactness of each connected region; and (3) a number that specifies the total number of connected regions that have been found. As before, the height of a region is measured along the lineal, and the width of a region is measured across the lineal. Also as before, in the connected component labeled color image, each pixel in the $m^{th}$ region found is assigned gray level m. The region property table is called undetermined_color_image.

The measures appearing in the undetermined_color_image table form the basis for an inexact descriptive vocabulary that will be used to classify the three remaining feature types. Conjunctions and disjunctions of this set of adjectives are used to describe the features. Fuzzy logic is once again used in making decisions. The fuzzy membership functions used are piece-wise linear, i.e., of the form shown in FIG. 6. Standard methods for assigning membership function values to the conjunctions, disjunctions, and complements are used as before.

The rule used to determine if an area of the color image is a crayon mark is as follows:
If a region is darker (fuzzy membership function based on relative_intensity) and if the region is bluer than clear wood (fuzzy membership function based on $\vec{o}$ dotted with (0, 0, 1)), then the region is a crayon mark.

Note that it is assumed that blue crayons are used to make the marks on this embodiment. However, this methodology can easily be modified by those skilled in the art to accommodate other colors of crayons as well.

Figures 7A, 7B:
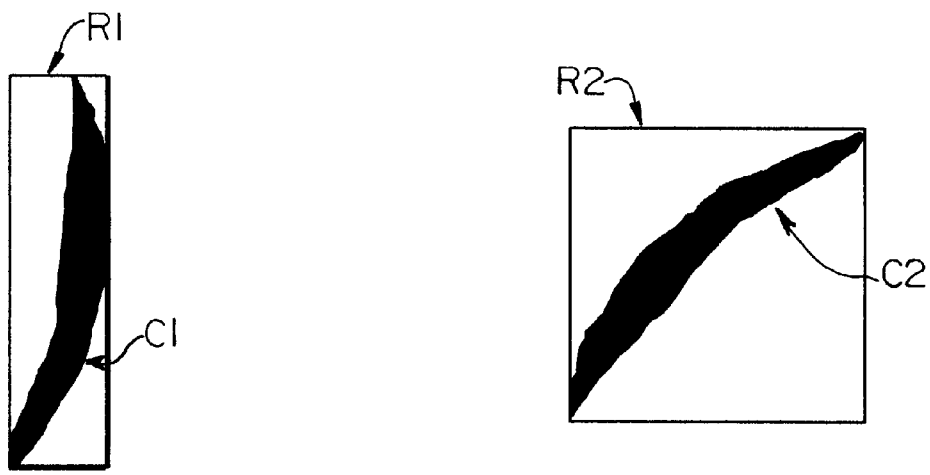
FIG. 7A illustrates a crack occurring along the wood grain, and the minimum inscribing rectangle for the crack.
FIG. 7B illustrates a crack occurring across the wood grain, and the minimum inscribing rectangle for the crack.

The rule used to determine if an area is a crack is based on three points of logic. First, a small crack always appears to be blacker than clear wood in the color image. Second, cracks usually occur along the wood grain as a separation of the wood grain, i.e., aligned along the length of the lineal. FIG. 7A illustrates a crack C1 occurring along the wood grain; the minimum inscribing rectangle for crack C1 is denoted as R1. In this instance, the height versus width ratio is large and the compactness is also large. Third, on occasion, cracks sometimes occur across the wood grain. FIG. 7B illustrates a crack C2 occurring across the wood grain; the minimum inscribing rectangle for crack C2 is denoted as R2. In this instance, the height versus width ratio is smaller and the compactness is also much smaller. Hence the rule for identifying cracks is:
[If the region is darker than clear wood (fuzzy membership function based on relative_intensity) and if the region is grayer than clear wood (fuzzy membership function based on the magnitude of vector that is the orthogonal projection of ($A_{red}$, $A_{green}$, $A_{blue}$) onto the plane defined by $\vec{w} \cdot \vec{x} = 0$ where $\vec{w} = (1/\sqrt{2}, 1/\sqrt{2}, 1/\sqrt{2})$)

and if the region is long and narrow running along the grain (fuzzy membership function based on compactness) then the region is a crack.]

OR

[If the region is darker than clear wood (fuzzy membership function based on relative_intensity) and if the region is grayer than clear wood (fuzzy membership function based on the magnitude of vector that is the orthogonal projection of ($A_{red}$, $A_{green}$, $A_{blue}$) onto the plane defined by $\vec{w}\cdot\vec{x}=0$ where $\vec{w}=(1/\sqrt{2}, 1/\sqrt{2}, 1/\sqrt{2})$) and if the region is long and narrow running across the grain (fuzzy membership function based on compactness) then the region is a crack.]

To identify areas of stain, a threshold value is used. If the difference, i.e., the Euclidean norm distance, between the average color of the region and ($Av_{red}$, $Av_{green}$, $Av_{blue}$) is greater than the threshold, then the region is labeled surface stain; otherwise, it is considered as being clear wood.

After all the above-described processing has been completed, undetermined_color_image should be empty, with all the connected components found during the connected component labeling operation having been assigned to a feature class or to the clear wood class. Once the processing of the color image is complete, all algorithms in the feature detection module are complete for the lineal face. Information is directed to the evaluation and control computer 234, including: (1) the minimum inscribing rectangle of the lineal; (2) the board width; (3) the number of features found; and (4) the feature table which defines the identity of each feature detected and the coordinates of the feature's minimum inscribing rectangle.

Modifications and variations of the above-described embodiments of the present invention are possible, as appreciated by those skilled in the art in light of the above teachings. For example, the apparatus 10 can be modified to accommodate materials substantially wider than lineals, such as plywood, particle board, flitches, or lumber, in a manner that will be understood by those of skill in the art. Also, the fuzzy logic rules can be tailored to accommodate the other applications, also in a manner that will be understood by those of skill in the art.

It is therefore to be understood that, within the scope of the appended claims and their equivalents, the invention may be practiced otherwise than as specifically described.

What is claimed is:

1. Apparatus for inspecting lumber to determine the presence and location of defects to optimize cutting of the lumber, said apparatus comprising:

first and second color cameras for imaging first and second faces of the lumber and generating color image data thereof;

optical scanning means for imaging the whole width of the lumber for generating image data of a profile of the lumber;

electro-magnetic scanning means for generating image data of internal features of the lumber;

means for generating histograms corresponding to the color image data and the internal features image data;

dynamic selecting means for dynamically selecting histogram threshold levels for each piece of lumber relative to a peak in each of the histograms representing clear wood;

data ordering means for analyzing the profile image data from said optical scanning means first, for analyzing the internal features image data from said electro-magnetic scanning means second to locate large defect regions, for analyzing the internal features image data from said electro-magnetic scanning means again to locate small defect regions, and for analyzing the color image data from said first and second cameras last; and data removing means for finding regions in the image data that are known to be defect areas based on the histogram threshold levels selected by said dynamic selecting means and removing them from all image data and their corresponding histograms once found.

2. The system of claim 1, further comprising filter means for filtering the color image data as it is collected to reduce the required volume of color image data while preserving suspect defect regions.

3. The apparatus of claim 1, wherein said electro-magnetic scanning means, said first and second color cameras, and said optical scanning means are arranged at different locations from each other, whereby said electro-magnetic scanning means, said first and second color cameras, and said optical scanning means start scanning the lumber at different times; and wherein said apparatus further comprises:

memory means for storing image data from said first and second color cameras, said optical scanning means, and said electro-magnetic scanning means;

pre-processing means for collecting image data from said first and second color cameras, said optical scanning means, and said electro-magnetic scanning means, synchronizing the image data as it is collected, and simultaneously transferring the data to said memory means; and registering means for registering the image date collected by said pre-processing means and stored in said memory means.

4. The apparatus of claim 1, wherein said data removing means includes means for cross-referencing the profile image data and the color image data with the internal features image data to measure attributes of the lumber and means for identifying suspect defect areas found from the internal features image data using the attributes measured using said means for cross-referencing.

5. The apparatus of claim 4, wherein said data removing means uses fuzzy logic to assign a defect class based on the measured attributes.

6. The apparatus of claim 1, further comprising:

a computer memory; and means for storing images into said computer memory such that said apparatus can image a piece of lumber and generate the image data therefor while simultaneously processing the image data generated by the imaging of a previous piece of lumber.

7. A method for inspecting lumber to determine the presence and location of defects to optimize cutting of the lumber, said method comprising the steps of:

(a) obtaining color image data for first and second faces of a piece of lumber;

(b) obtaining profile image data for the whole width of the lumber;

(c) obtaining image data of internal features of the lumber;

(d) generating histograms corresponding to the color image data and the internal features data;

(e) analyzing the profile image data using a computer processor;

(f) dynamically selecting histogram threshold levels for the lumber relative to a peak representing clear wood in each of the histograms for the internal features image data;

(g) following said steps (e) and (f), analyzing the internal features image data using the computer processor to locate large defect regions based on the analysis of the profile image data from said step (e) and based on the histogram threshold levels selected in said step (f) and removing the large defect regions so located from all the image data and their corresponding histograms;

(h) following said step (g), dynamically selecting histogram threshold levels for the lumber relative to a peak representing clear wood in each of the histograms for the internal features image data as modified in said step (g);

(i) following said step (h) analyzing the internal features image data again using the computer processor to locate small defect regions including finding regions, in the internal features image data that are known to be defect areas based on the histogram threshold levels selected in said step (h) and once found, removing them from all the image data and their corresponding histograms as modified in said step (g);

(j) following said step (i), dynamically selecting histogram threshold levels for the lumber relative to a peak representing clear wood in each of the histograms for the color image data as modified in said step (i);

(k) following said step (j), analyzing the color image data using the computer processor, including finding regions in the color image data that are known to be defect areas based on the histogram threshold levels for the color image data selected in said step (j); and (l) using the analysis of of said steps (e), (g), (i), and (k) to optimize cutting of the lumber.

8. The method of claim 7, wherein said step (e) includes identifying areas with insufficient thickness, and wherein said step (g) includes removing the areas of insufficient thickness identified in said step (f) from all of the histograms generated in said step (d).

9. The method of claim 8, wherein said steps (g) and (i) include identifying areas which are less dense than clear wood, and removing the less dense areas from all of the image data and their corresponding histograms.

10. The method of claim 9, further comprising the step of using a crack/check preserving filter to reduce the number of color pixels to be stored and analyzed, prior to said step (d).

11. The method of claim 10, wherein said step of using a crack/check preserving filter comprises:

creating disjoint N×M sub-arrays of the color image data which in totality completely cover the color image, each point in the N×M sub-arrays representing a color pixel;

finding the color pixel in each N×M sub-array that has the darkest color; and choosing the darkest color in each N×M sub-array to represent the whole N×M sub-array.

12. The method of claim 7, wherein said step (g) is performed using a histogram-based segmentation procedure including the steps of:

smoothing the histograms corresponding to the internal features data;

looking for inflection points in the smoothed histograms of the internal features image data;

using the inflection points to detect large features; and removing the effects of the detected large features from the smoothed histograms to create modified histogram data; and wherein said step (i) includes using the modified histogram data to detect smaller wood features.

13. The method of claim 7, wherein said steps (g) and (i) include cross-referencing the profile image data and the color image data with the internal features image data to measure attributes of the lumber and identifying suspect defect regions found from the internal features image data using the measured attributes.

14. The method of claim 7, wherein said steps (g), (i), and (k) are carried out using a segmentation procedure and a connected-component labeling algorithm.

15. The method of claim 7, wherein in said steps (g) and (i), said analyzing is performed using fuzzy concepts to define feature classes for the lumber.

16. Apparatus for inspecting a wood object to determine the presence and location of defects in the object, said apparatus comprising:

means for generating color image data representing surface features of an object;

means for generating profile image data representing the three-dimensional shape of the object;

means for generating x-ray image data representing internal features of the object;

first and second feature detecting computers to process the color, profile, and x-ray image data and locate defects, said first computer processing information obtained from a first surface of the object and said second computer processing information obtained from a second surface of the object, said first and second computers each including a memory;

means for registering the color image data, the profile image data, and the x-ray image data by establishing a common coordinate system in two-dimensional space and by ensuring that the spatial resolution of each set of image data is the same;

means for generating histograms corresponding to the color image data, the profile image data, and the x-ray image data;

means for analyzing the color image data, the profile image data, and the x-ray image data using a histogram-based segmentation procedure to produce a respective segmented profile image, segmented color image, and segmented x-ray image;

means for finding regions in each of the segmented profile, color, and x-ray images that are known to be defect areas by applying a connected component labeling algorithm to each of the segmented profile, color, and x-ray images and for removing the defect areas from each of the segmented profile, color, and x-ray images and its corresponding histogram, once found;

means for ordering the analysis of the segmented profile, camera, and x-ray image data to decrease the volume of data that must be analyzed by: first processing the profile data to locate areas of insufficient thickness, removing areas of insufficient thickness from the x-ray image data and then analyzing the remaining x-ray image data to locate areas of less density, removing areas of insufficient thickness and less density from the color image data and then analyzing the remaining color image data to confirm defects having both surface and internal features;

image preprocessing means for preprocessing the image data from said means for generating color image data, said means for generating profile image data, and said means for generating x-ray image data, said preprocessing including synchronizing of the image data as it is collected; and interface means for transferring image data from each of said means for generating color image data, said means for generating profile image data, and said means for generating x-ray image data into computer memory in a standard direct memory access method so that no CPU intervention is required and for filtering the color image data as it is collected using a crack-preserving filter to reduce the resolution of the volume of the color image data while preserving the level of detail needed to locate and identify small cracks.

17. The apparatus of claim 16, wherein the histogram-based segmentation procedure used by said analyzing means considers the largest peak in the histogram to be caused by the characteristics of clear wood, and looks for deviations from these characteristics by looking for inflection points in a smoothed histogram.

18. The apparatus of claim 16, further comprising an integrated evaluation and control computer for processing object feature locations, identities, and characteristics passed to it by said first and second computers for formulating a strategy for sawing the object based on the defects located by said first and second feature detecting computers.

19. The apparatus of claim 16, further comprising:

a computer memory; and means for storing images into said computer memory such that said apparatus can generate the image data for one object while simultaneously processing the image data generated in connection with a previous object.

* * * * *